United States Patent [19]
Calenoff

[11] Patent Number: 5,763,164
[45] Date of Patent: Jun. 9, 1998

[54] IMMUNOGENIC CANCER PROTEINS AND PEPTIDES AND METHODS OF USE

[75] Inventor: Emanuel Calenoff, Chicago, Ill.

[73] Assignee: Northwestern University, Evanston, Ill.

[21] Appl. No.: 191,338

[22] Filed: Feb. 3, 1994

Related U.S. Application Data

[63] Continuation-in-part of Ser. No. 49,698, Apr. 16, 1993, abandoned.

[51] Int. Cl.[6] .................. C12Q 1/68; G01N 33/53; C07K 15/28; C07H 21/02
[52] U.S. Cl. .................. 435/6; 435/5; 435/7.1; 435/7.2; 435/7.9; 435/69.1; 530/300; 530/388.1; 530/387.2; 530/350; 530/333; 530/403; 436/500; 436/548; 436/818; 424/1.11; 536/23.1
[58] Field of Search .................. 435/6, 5, 7.1–7.9, 435/69.1; 530/300, 388.1, 350, 387.2, 333, 403; 436/500, 548, 818; 424/1.11

[56] References Cited

U.S. PATENT DOCUMENTS

| | | | |
|---|---|---|---|
| 4,399,216 | 8/1983 | Axel et al. | |
| 4,458,066 | 7/1984 | Caruthers et al. | 536/27 |
| 5,382,513 | 1/1995 | Lam et al. | 435/7.1 |
| 5,532,167 | 7/1996 | Cantley et al. | |

OTHER PUBLICATIONS

Beaucage, et al. *Tetrahedron Letters* 22: 1859–1862 (1981).
Berczi et al. "Tumor–Reactive IgE Antibodies in Plasma of Patients with Gastrointestinal Carcinomas", *Cancer Immunol Immunother* 14:180–184 (1983).
W. Neal Burnette "Western Blotting: Electrophoretic Transfer of Proteins from Sodium Dodecyl Sulfate—Polyacrylamide Gels to Unmodified Nitrocellulose and Radiographic Detection with Antibody and Radioiodinated Protein A", *Anal. Biochem.* 112:195–203 (1981).
Ceska et al. "Radioimmunosorbent Assay of Allergens", *J. of Allergy and Clin. Imm.* 49:1–9 (1972).
Cheever I et al. "Specific Adoptive Therapy of Established Leukemia with Syngeneic Lymphocytes Sequentially Immunized In Vivo and In Vitro and Non Specifically Expanded By Culture with Interleukin 2", *J. of Immun.* 126:1318–1322 (1981).
Cheever II et al. "Augmentation of the Anti–Tumor Therapeutic Efficacy of Long–Term Cultured T Lymphocytes By In Vivo Administration of Purified Interleukin 2", *J. of Med.* 155:968–980 (1982) 2 Exp. Med.
Cheever III et al. "Review: Potential for Specific Cancer Therapy with Immune T Lymphocytes", *J. of Biol. Resp. Mod.* 3:113–127 (1984).
Cheever IV et al. "Interleukin–2 Administered In Vivo Induces the Growth and Augments the Function of Cultured T Cells In Vivo", *J. of Biol. Resp. Med.* 3:462–467 (1984).
Cheever V et al. "Interleukin 2 Administered In Vivo Induces the Growth of Cultured T. Cells *In Vivo*", *J. of Imm.* 132:2259–2265 (1984).
Cheever VI et al., "Interleukin 2 (IL2) Administered In Vivo: Influence of IL2 and Timing of T Cell Growth", *J. of Imm.* 134:3895–3899 (1985).
Cheever VII et al. "Antigen Driven Long Term Cultured T Cells Proliferate In Vivo Distribute Widely, Medicate Specific Tumor Therapy, and Persist Long Term as Functional Memory T Cells", *J. Exp. Med.* 163:1100–1112 (1986).
Graziani et al., "The Human dbl–proto–oncogene Product is a Cytoplasmic Phosphoprotein which is Associated with the Cytoskeletal Matrix," *Oncogene*, 4:823–829, 1989.
Ron et al., "Molecular Cloning and Characterization of the Human dbl Proto–oncogene: Evidence that its Overexpression is Sufficient to Transform NIH/3T3 Cells," *EMBO Journal*, 7:2465–2473, 1988.
Srivastava et al., "Identification of the Protein Encoded by the Human Diffuse B–cell Lymphoma (dbl) Oncogene," *Proc. Natl. Acad. Sci.*, 83:8868–8872, 1986.
Eva et al., "The Predicted DBL Oncogene Product Defines a Distinct Class of Transforming Proteins," *Proc. Natl Acad. Sci.*, 85:2061–2065, 1988.
Pickering et al., "Human Monoclonal Antibodies to Cytokeratins Associated with Squamous Cells Carcinoma," *Clinical Immunology Immunopathology*, 32:253–260, 1984.
Ioannides et al., "Cytotoxic T Cells Clones Isolated form Ovarian Tumor–Infiltrating Lymphocytes Recognize Multiple Antigenic Epitopes on Autologous Tumor Cells," *Journal Immunology*, 146:1700–1707, 1991.
Ben–Mahrez, "Detection of Circulating Antibodies Against c–myc Protein in Cancer Patient Sera," *British Journal Cancer*, 57:529–534, 1988.
Sorokine et al., "Presence of Circulating Anti–c–myb Oncogene Product Antibodies in Human Sera," *International Journal Cancer*, 47:665–669, 1991.
Davidoff et al., "Immune Response to p53 is Dependent upon p53/HSP70 Complexes is Breast Cancers," *Proc. Natl. Aca. Sci.*, 89:3439–3442, 1992.
Dillner et al, PNAS 886: 3838–3841, 1989.
Van Der Bruggen et al., Science, 254: 1643–1647, 1991.

*Primary Examiner*—W. Gary Jones
*Assistant Examiner*—Dianne Rees
*Attorney, Agent, or Firm*—Brinks Hofer Gilson & Lione

[57] ABSTRACT

The present invention relates to tumor specific antigens and functional proteins of a tumor cell preparable by identifying protein presents in the tumor cell that are selectively immunogenic for tumor patients. The present invention still further provides a process of making a peptide library of tumor specific humoral antigens, a process of increasing the immunogenic specificity of a tumor-associated antigen, an assay kit for detecting the presence of an antibody immunoreactive with a tumor-specific antigen, and a process of making T cells sensitized to a tumor-specific antigen.

11 Claims, 13 Drawing Sheets

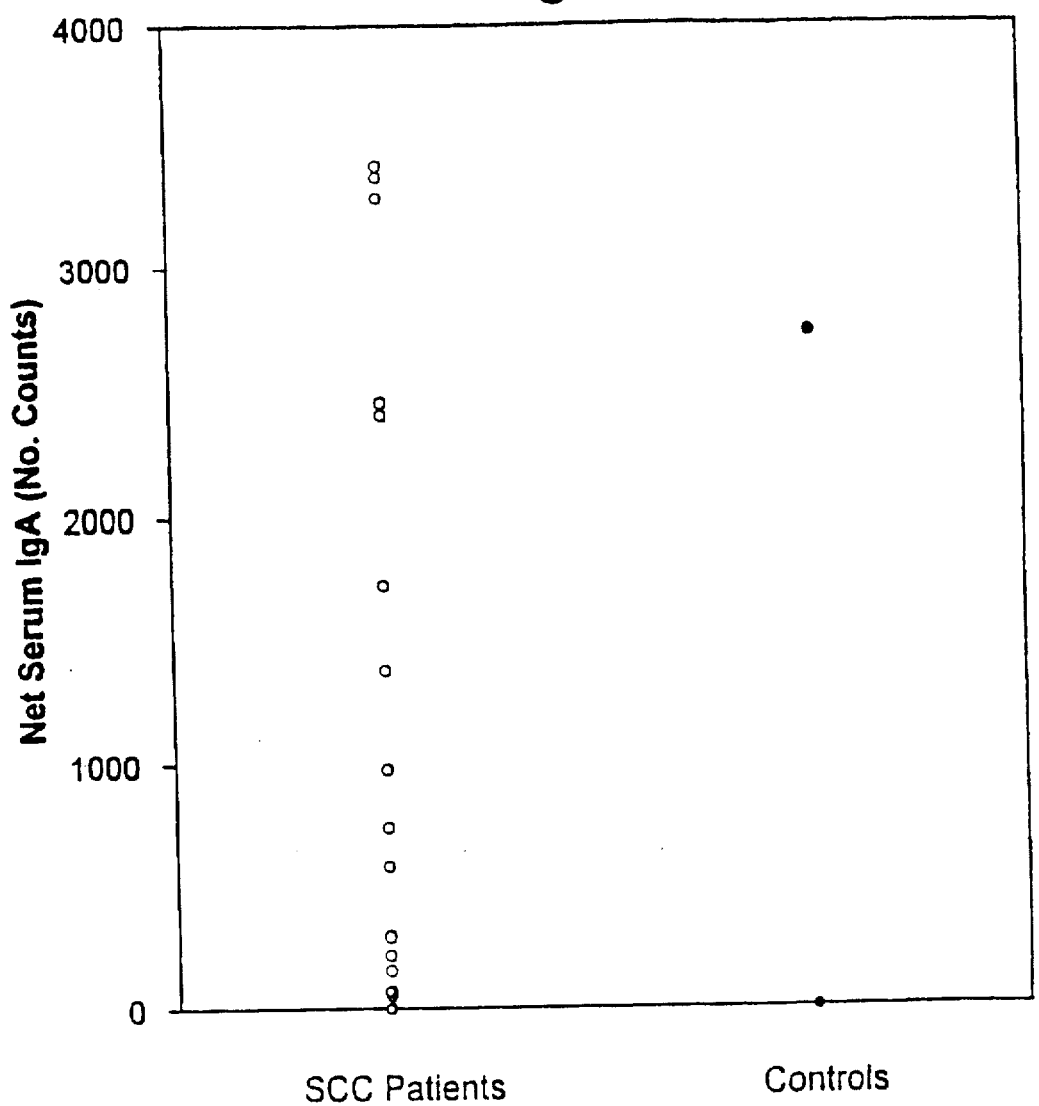

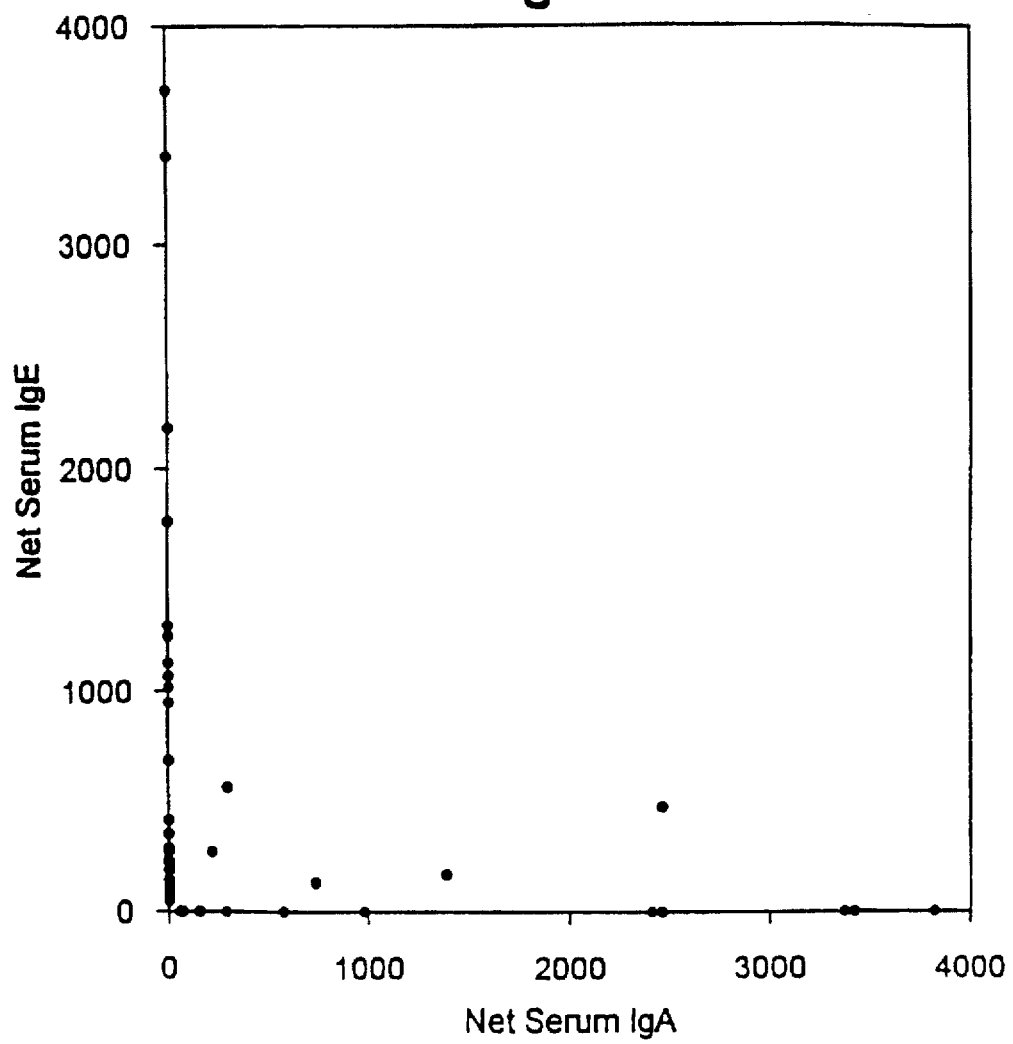

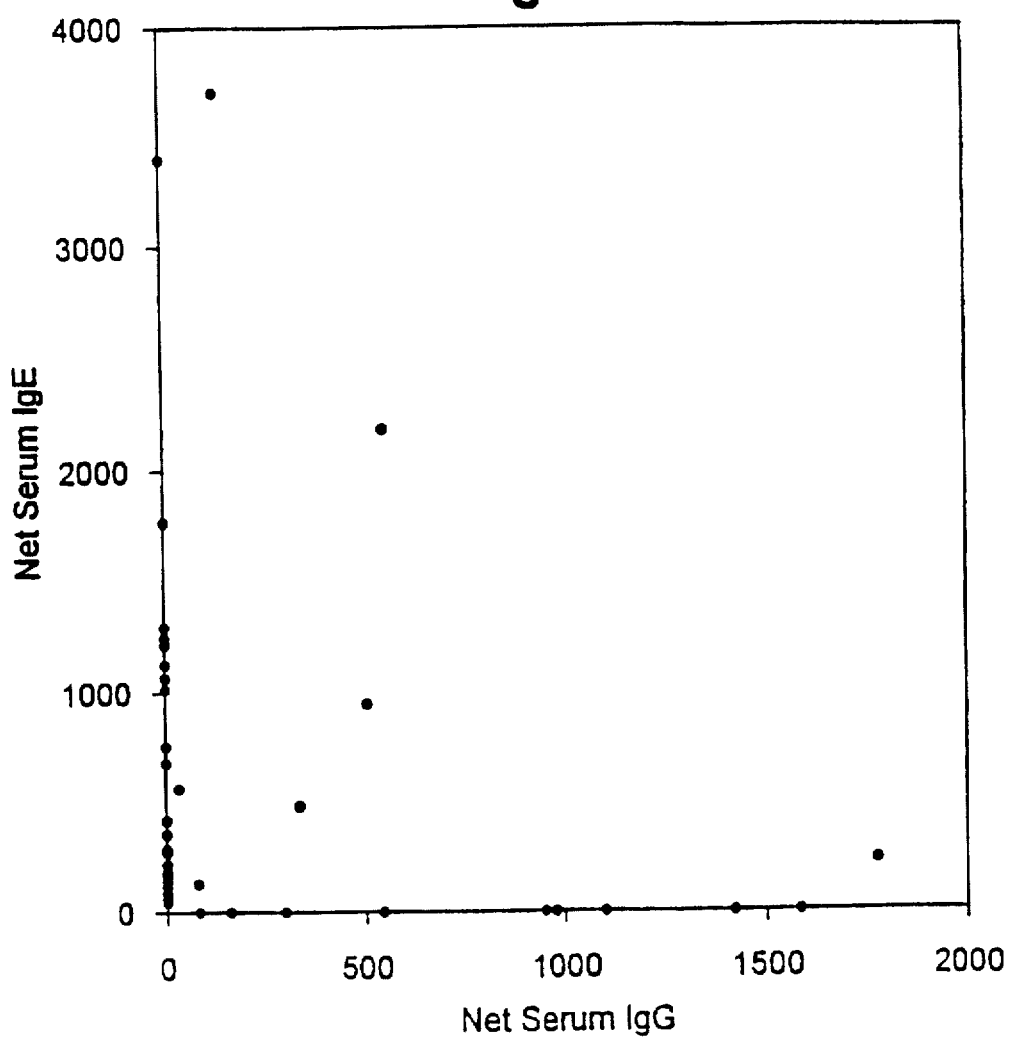

Fig. 5A

| | 3.3 | 16.1 | 16.3 | 16.4 | 27.3 | 35.1 | 35.2 | 37.1 | 37.2 | 39.1 | 39.2 | 39.4 |
|---|---|---|---|---|---|---|---|---|---|---|---|---|
| Mol. Wt. (K) | 63 | 71 | 61 | 52 | 10 | 230 | 56 | 78 | 69 | 280 | 220 | 8 |
| SCC Patients: | | | | | | | | | | | | |
| DS | + | - | - | + | - | + | - | + | + | + | + | - |
| JS | | - | - | + | + | + | + | - | - | + | + | + |
| KR | | - | - | - | - | + | + | - | + | - | - | - |
| KY | + | - | - | - | + | + | - | - | + | + | + | + |
| LN | + | - | - | - | + | + | - | - | + | - | - | - |
| SI | + | - | + | - | - | + | - | - | + | - | - | - |
| H/N #52 | | - | - | - | + | + | - | - | - | | | |
| H/N #74 | | + | - | - | | | | | | | | |
| H/N #114 | | | | | + | + | - | - | - | + | + | - |
| H/N #202 | - | | | | + | | | | | - | - | + |
| H/N #357 | + | - | - | - | | + | - | | | - | + | + |
| H/N #469 | | | | | + | | | | | - | + | + |
| H/N #627 | - | - | + | - | | + | - | | | | | |
| Controls: | | | | | | | | | | | | |
| CL | - | - | - | - | - | - | - | - | - | - | - | - |
| DE | - | - | - | - | - | - | - | - | - | - | - | - |
| HS | - | - | - | - | - | - | + | - | - | - | - | - |
| LI | - | - | - | - | - | - | - | - | - | - | - | - |
| MI | - | - | - | - | - | - | - | - | - | - | - | - |
| PE | - | - | - | - | - | - | - | - | - | - | - | - |
| PS | - | - | - | - | - | - | - | - | - | - | - | - |
| RB | - | - | - | - | - | - | - | - | - | - | - | - |
| SK | - | - | - | - | - | - | - | - | - | - | - | - |
| SA | - | - | - | - | - | - | - | - | - | - | - | - |

Fig. 5B

| | 40.1 | 40.3 | 40.4 | 47.2 | 47.3 | 47.4 | 49.1 | 49.2 | 49.3 | 50.1 | 50.2 | 50.3 |
|---|---|---|---|---|---|---|---|---|---|---|---|---|
| Mol. Wt. (K) | 105 | 59 | 49 | 205 | 62 | 54 | 260 | 57 | 8 | 61 | 54 | 37 |
| SCC Patients: | | | | | | | | | | | | |
| DS | - | + | - | - | + | - | - | + | - | + | - | - |
| JS | - | - | - | - | - | + | + | + | - | + | - | - |
| KR | - | + | + | - | + | - | - | + | - | + | - | - |
| KY | - | + | - | - | + | + | + | + | - | + | + | - |
| LN | - | - | - | - | - | - | + | - | - | + | - | + |
| SI | - | + | - | - | + | - | - | - | - | + | + | - |
| H/N #52 | | | | | - | - | + | | | | | |
| H/N #74 | - | + | + | - | - | + | | | | - | + | - |
| H/N #114 | - | - | - | | | | + | - | - | | | |
| H/N #202 | | | | - | - | + | + | - | - | + | + | - |
| H/N #357 | | | | | | | | | | | | |
| H/N #469 | - | - | - | | | | + | - | - | - | - | - |
| H/N #627 | + | - | - | + | - | + | + | - | + | - | + | - |
| Controls: | | | | | | | | | | | | |
| CL | - | - | - | - | - | - | + | - | - | - | - | - |
| DE | - | - | - | - | - | - | - | - | - | - | - | - |
| HS | - | - | - | - | - | - | + | - | - | - | - | - |
| LI | - | - | - | - | - | - | - | - | - | - | - | - |
| MI | - | - | - | - | - | - | - | - | - | - | - | - |
| PE | - | - | - | - | - | - | - | - | - | - | - | - |
| PS | - | - | - | - | - | - | - | - | - | - | - | - |
| RB | - | - | - | - | - | - | - | - | - | - | - | - |
| SK | - | - | - | - | - | - | - | - | - | - | - | - |
| SA | - | - | - | - | - | - | - | - | - | - | - | - |

FIG. 6

| | dbl | erbB-1 | erbB-2 | erbB-3 | fos | fyn | USP70 | cjun | lck | lyn | p13 | p190 | rapGAP | ras | rasGAP | yes |
|---|---|---|---|---|---|---|---|---|---|---|---|---|---|---|---|---|
| Cancer Pts. | | | | | | | | | | | | | | | | |
| 284 | + | . | . | . | . | . | . | + | . | . | . | . | . | + | . | + |
| 581 | + | . | . | . | . | . | . | + | + | . | . | + | . | . | + | + |
| 737 | + | . | + | . | + | . | . | + | + | . | + | . | . | + | + | + |
| 936 | + | . | . | . | . | + | . | + | + | . | + | + | . | . | + | . |
| 1068 | . | . | . | . | + | . | . | + | . | . | . | + | + | + | + | . |
| 1189 | . | . | + | . | . | . | . | + | . | . | . | + | . | . | + | + |
| 1200 | . | . | . | . | . | . | . | . | . | . | . | . | . | . | . | . |
| 1249 | . | . | . | . | . | . | . | . | . | . | . | . | . | . | + | . |
| 2371 | . | . | . | . | . | . | . | + | . | . | . | . | . | + | + | + |
| 2771 | + | . | . | . | . | . | . | . | . | . | . | . | . | + | + | + |
| D.C. | . | . | + | . | . | . | . | . | + | . | . | . | . | . | . | . |
| E.E. | . | . | . | . | . | . | . | . | . | . | . | . | . | . | . | . |
| H.P. | . | . | . | . | + | + | + | + | . | . | . | . | + | . | + | . |
| L.M. | + | . | + | . | + | . | . | . | . | . | . | . | . | + | . | . |
| R.P. | . | . | . | . | + | + | + | . | . | . | . | + | + | . | + | + |
| Benign Pts. | | | | | | | | | | | | | | | | |
| S.C. | . | . | . | . | . | . | . | + | + | . | . | . | + | + | . | + |
| W.H. | . | . | . | . | . | . | . | + | + | . | + | . | + | + | . | + |
| W.B. | + | . | . | . | . | . | . | + | + | . | + | . | + | + | + | + |
| L.R. | . | . | + | . | + | + | + | . | . | + | . | + | + | . | . | + |
| D.D. | . | . | . | . | . | . | . | . | . | . | . | . | . | + | . | + |
| S.D. | . | . | . | . | . | . | . | + | . | . | + | . | + | . | + | . |
| K.B. | . | . | . | . | . | . | . | . | + | . | . | . | + | . | . | . |
| P.T.H. | . | . | . | . | . | . | . | + | . | . | . | + | . | . | . | . |
| A.N. | . | . | . | . | . | . | . | . | . | . | . | + | . | . | . | . |
| P.K. | . | . | . | . | . | . | . | . | . | . | . | . | . | . | . | . |
| R.P. | . | . | . | . | + | . | . | . | . | . | . | + | + | + | + | + |
| B.B. | . | . | . | . | . | . | . | . | . | . | . | . | + | . | . | + |
| A.J. | . | . | . | . | . | + | + | + | . | . | . | . | + | + | + | . |
| G.J. | . | . | + | . | . | . | . | + | . | . | . | . | + | + | + | . |
| K.L. | . | . | . | . | . | . | . | . | . | . | . | . | . | . | + | . |

|  | POS/NEG | | SIGNAL | | |
|---|---|---|---|---|---|
|  | IgA | IgG | IgA | IgG | Total Signal |
| Cancer Pts. | | | | | |
| 284 | + | + | 19 | 100 | 119 |
| 581 | + | . | 8 | . | 8 |
| 737 | + | . | 16 | . | 16 |
| 936 | + | . | 100 | . | 100 |
| 1068 | . | . | . | . | . |
| 1189 | . | . | . | . | . |
| 1200 | . | . | . | . | . |
| 1249 | . | . | . | . | . |
| 2371 | . | . | . | . | . |
| 2771 | + | + | 16 | 70 | 86 |
| D.C. | . | . | . | . | . |
| E.E. | . | . | . | . | . |
| H.P. | . | . | . | . | . |
| L.M. | + | + | 56 | 73 | 129 |
| R.P. | . | . | . | . | . |
| Benign Pts. | | | | | |
| S.C. | . | . | . | . | . |
| W.H. | . | . | . | . | . |
| W.B. | + | . | 15 | . | 15 |
| L.R. | . | . | . | . | . |
| D.D. | . | . | . | . | . |
| S.D. | . | . | . | . | . |
| K.B. | . | . | . | . | . |
| P.T.H. | . | . | . | . | . |
| A.N. | . | . | . | . | . |
| P.K. | . | . | . | . | . |
| R.P. | . | . | . | . | . |
| B.B. | . | . | . | . | . |
| A.J. | . | . | . | . | . |
| G.J. | . | . | . | . | . |
| K.L. | . | + | . | 24 | 24 |

FIG. 7

|  | FT | 2+3 | FT Spiking |
|---|---|---|---|
| Cancer Pts. | | | |
| 284 | + | + | . |
| 581 | + | + | . |
| 737 | + | + | . |
| 936 | + | + | + |
| 1068 | + | + | . |
| 1189 | + | . | . |
| 1200 | . | . | . |
| 1249 | . | . | . |
| 2371 | + | . | . |
| 2771 | + | + | + |
| D.C. | . | . | . |
| E.E. | . | . | . |
| H.P. | + | + | + |
| L.M. | + | + | + |
| R.P. | . | . | . |
| Benign Pts. | | | |
| S.C. | . | . | . |
| W.H. | . | . | . |
| W.B. | + | + | . |
| L.R. | + | + | . |
| D.D. | . | . | . |
| S.D. | . | . | . |
| K.B. | + | . | . |
| P.T.H. | . | . | . |
| A.N. | + | + | . |
| P.K. | . | . | . |
| R.P. | + | + | . |
| B.B. | . | . | . |
| A.J. | + | . | . |
| G.J. | + | . | . |
| K.L. | + | . | . |

FIG. 8

| | Stage I Ductal CA | Stage II Ductal CA | Stage III Ductal CA | Stage IV Ductal CA |
|---|---|---|---|---|
| Samples Tested | 20 | 29 | 3 | 2 |
| IgA-reactive [% positive] | 3 [15] | 4 [14] | 1 [33] | 1 [50] |
| IgG-reactive [% positive] | 1 [5] | 4 [14] | 0 [0] | 0 [0] |
| IgA+IgG-reactive [%] | 4 [20] | 7 [24] | 1 [33] | 1 [50] |

| | Lobular CA (all stages) | Benign Br. Lesions | Healthy Controls |
|---|---|---|---|
| Samples Tested | 5 | 27 | 36 |
| IgA-reactive [% positive] | 1 [20] | 1 [4] | 1 [3] |
| IgG-reactive [% positive] | 0 [0] | 0 [0] | 0 [0] |
| IgA+IgG-reactive [%] | 1 [20] | 1 [4] | 1 [3] |

| | | | | |
|---|---|---|---|---|
| ABL | CYCLIN B1/B2 | FRA-2 | MAP | RAB |
| ACTIVIN A | DBL | FYN | MAPK | RAC |
| ACTIVIN B | DEPHOSPHIN | GAP-43 | MAPKAP | RAF-1 |
| ACTIVIN AB | DNA-PK | GAP-ASSOC.P62 | MAPKKs | RAG-2 |
| AKT | E2F | GAP-ASSOC.P190 | MARCKS | RAL |
| ALPHA Q | E7 (HPV) | GAS2 | MAX | RALGAP |
| ANP3 | ELF-2 | GDI | MEK 1 | RAP |
| AP-1 | ELF-1 | GDS | MEK 2 | RAP1B.GAP |
| ARF | ELK-1 | GEPHYRIN | MEKK | RAS |
| ARG | ELK-2 | GEPS | MEL-18 | RASGAP |
| ATF-1 | ENOLASE | Gq APLPHA | MET | RB |
| 21B | ENV-SEA | GLI | MIP | REL |
| B-50 | EPS15 | GLUCOCORTICOID-R | MKK-2 | RET |
| BCR | ERBA-ALPHA | GRB-2 | MOS | RETINOIC ACID-R |
| BCR/ABL | ERBA-BETA | GSP | MOSXE | RHO |
| BCL-2 | ERBB-1 | GST/PIM | MYB | RHOM-2 |
| BCL3 | ERBB-2 (NEU) | HCK | MYC | ROS |
| BEK (FGF-R2) | ERBB-3 | HGF | MYOGENIN | RPB1 |
| BLK | ERG | HOX2.4 | NCK | SEM-5 |
| BMI-1 | ESTROGEN-R | HST-1 (GFG) | NF-1-GAP | SHC |
| BNP | ERG-2 | HST-2 (FGF) | NF-AT B | SKI |
| CALDESMON | ERK1 | INHIBIN A | NF-KAPPA B | SMG |
| CALPECTIN | ERK2 | INHIBIN B | NM 23 | SNO N |
| CAM KINASE I | ERK3 | MIS | NUMATRIN | SOS 1 |
| CAM KINASE II | ERK4 | L-KAPPA B | ONCOPROTEIN 18 | SPI-1 |
| CAM KINASE III | ETS-1 | INT-1 | P6 INSULIN GFR | SPF |
| BETA-CASEIN | ETS-2 | INT-2 | P52 | SRC |
| CASEIN KINASE I | EVI-1 | INT-3 | P53 | SYP |
| CASEIN KINASE II | F-52 | IP-1 | P107 | TAL-1/SCI |
| CBL | FAK | IRS-1 | P120 | TCL-3/HOX11 |
| CDC2 | FER | JAK1 | PBX | TCF |
| CDK2 | FES | JAK2 | PDGF-R | TEC PTK |
| CDK3 | FGF (BASIC) | JUN | PL3 | TIK |
| CDK4 | FGFR4 | KIT(SLF-R) | PAXILLIN | TRK A |
| CONNEXIN-31 | FGR | LAMIN A | PIM/GST | TRK B |
| CONNEXIN-32 | FLG (FGF-R1) | LAMIN B | PKA | TRK C |
| CONNEXIN-43 | FLK | LCK | PKC-ALPHA | TTG/RHOM-1 |
| CREM-ALPHA | FLT-1,2 | LIPOCORTIN | PKC-BETA 1 | YES |
| CREM-BETA | FMS (CSF-R) | LYL-L | PKC-GAMMA | YRK |
| CREB | FOS | LYN | PLC-GAMMA 1 | VAV |
| CRK | FPS | MAD3 | PLC-GAMMA 2 | VIMENTIN |
| CSK | FRA-1 | MAF | PRAD-1 | VITAMIN D-R |

FIG. 11

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

```
Gln  Phe  Pro  Phe  Gly  Ala  Gly  Glu  Thr
1                    5
```

( 2 ) INFORMATION FOR SEQ ID NO:2:

( i ) SEQUENCE CHARACTERISTICS:
      ( A ) LENGTH: 477 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

```
Met  Ser  Ser  Gly  Arg  Arg  Arg  Gly  Ser  Ala  Pro  Trp  His  Ser  Phe  Ser
1                 5                    10                         15

Arg  Phe  Phe  Ala  Pro  Arg  Ser  Pro  Ser  Arg  Asp  Lys  Glu  Glu  Glu  Glu
                 20                    25                         30

Glu  Glu  Arg  Pro  Gly  Thr  Ser  Pro  Pro  Ala  Pro  Gly  Arg  Ser  Ala
           35                    40                    45

Ala  Ser  His  Val  Leu  Asn  Glu  Leu  Ile  Gln  Thr  Glu  Arg  Val  Tyr  Val
     50                    55                    60

Arg  Glu  Leu  Tyr  Thr  Val  Leu  Leu  Gly  Tyr  Arg  Ala  Glu  Met  Asp  Asn
65                    70                    75                         80

Pro  Glu  Met  Phe  Asp  Leu  Met  Pro  Pro  Leu  Leu  Arg  Asn  Lys  Lys  Asp
                 85                    90                         95

Ile  Leu  Phe  Gly  Asn  Met  Ala  Glu  Ile  Tyr  Glu  Phe  His  Asn  Asp  Ile
                 100                   105                        110

Phe  Leu  Ser  Ser  Leu  Glu  Asn  Cys  Ala  His  Ala  Pro  Glu  Arg  Val  Gly
                 115                   120                        125

Pro  Cys  Phe  Leu  Glu  Arg  Lys  Asp  Asp  Phe  Gln  Met  Tyr  Ala  Lys  Tyr
     130                   135                        140

Cys  Gln  Asn  Lys  Pro  Arg  Ser  Glu  Thr  Ile  Trp  Arg  Lys  Tyr  Ser  Glu
145                       150                   155                        160

Cys  Ala  Phe  Phe  Gln  Glu  Cys  Gln  Arg  Lys  Leu  Lys  His  Arg  Leu  Arg
                 165                   170                        175

Leu  Asp  Ser  Tyr  Leu  Leu  Lys  Pro  Val  Gln  Arg  Ile  Thr  Lys  Tyr  Gln
                 180                   185                        190
```

| Leu | Leu | Leu | Lys | Glu | Leu | Leu | Lys | Tyr | Ser | Lys | Asp | Cys | Glu | Gly | Ser |
|     |     | 195 |     |     |     |     | 200 |     |     |     | 205 |     |     |     |     |

| Ala | Leu | Leu | Lys | Lys | Ala | Leu | Asp | Ala | Met | Leu | Asp | Leu | Leu | Lys | Ser |
|     | 210 |     |     |     |     | 215 |     |     |     |     | 220 |     |     |     |     |

| Val | Asn | Asp | Ser | Met | His | Gln | Ile | Ala | Ile | Asn | Gly | Tyr | Ile | Gly | Asn |
| 225 |     |     |     |     | 230 |     |     |     |     | 235 |     |     |     |     | 240 |

| Leu | Asn | Glu | Leu | Gly | Lys | Met | Ile | Met | Gln | Gly | Gly | Phe | Ser | Val | Trp |
|     |     |     |     | 245 |     |     |     |     | 250 |     |     |     |     | 255 |     |

| Ile | His | Lys | Lys | Gly | Ala | Thr | Lys | Met | Lys | Asp | Leu | Ala | Arg | Phe | Lys |
|     |     |     | 260 |     |     |     |     | 265 |     |     |     |     | 270 |     |     |

| Pro | Met | Gln | Arg | His | Leu | Phe | Leu | Tyr | Glu | Lys | Ala | Ile | Val | Phe | Cys |
|     |     | 275 |     |     |     |     | 280 |     |     |     |     | 285 |     |     |     |

| Lys | Arg | Arg | Val | Glu | Ser | Gly | Glu | Gly | Ser | Asp | Arg | Tyr | Pro | Ser | Tyr |
|     |     | 290 |     |     |     | 295 |     |     |     |     | 300 |     |     |     |     |

| Ser | Phe | Lys | His | Cys | Trp | Lys | Met | Asp | Glu | Val | Gly | Ile | Thr | Glu | Tyr |
| 305 |     |     |     |     | 310 |     |     |     |     | 315 |     |     |     |     | 320 |

| Val | Lys | Gly | Asp | Asn | Arg | Lys | Phe | Glu | Ile | Trp | Tyr | Gly | Glu | Lys | Glu |
|     |     |     |     | 325 |     |     |     |     | 330 |     |     |     |     | 335 |     |

| Glu | Val | Tyr | Ile | Val | Gln | Ala | Ser | Asn | Val | Asp | Val | Lys | Met | Thr | Trp |
|     |     |     | 340 |     |     |     |     | 345 |     |     |     |     | 350 |     |     |

| Leu | Lys | Glu | Ile | Arg | Asn | Ile | Leu | Leu | Lys | Gln | Gln | Glu | Leu | Leu | Thr |
|     |     | 355 |     |     |     |     | 360 |     |     |     |     | 365 |     |     |     |

| Val | Lys | Lys | Arg | Lys | Gln | Gln | Asp | Gln | Leu | Thr | Glu | Arg | Asp | Lys | Phe |
|     | 370 |     |     |     |     | 375 |     |     |     |     | 380 |     |     |     |     |

| Gln | Ile | Ser | Leu | Gln | Gln | Asn | Asp | Glu | Lys | Gln | Gln | Gly | Ala | Phe | Ile |
| 385 |     |     |     |     | 390 |     |     |     |     | 395 |     |     |     |     | 400 |

| Ser | Thr | Glu | Glu | Thr | Glu | Leu | Glu | His | Thr | Ser | Thr | Val | Val | Glu | Val |
|     |     |     |     | 405 |     |     |     |     | 410 |     |     |     |     | 415 |     |

| Cys | Glu | Ala | Ile | Ala | Ser | Val | Gln | Ala | Glu | Ala | Asn | Thr | Val | Trp | Thr |
|     |     |     | 420 |     |     |     |     | 425 |     |     |     |     | 430 |     |     |

| Glu | Ala | Ser | Gln | Ser | Val | Glu | Ile | Ser | Glu | Glu | Pro | Ala | Glu | Trp | Ser |
|     |     | 435 |     |     |     |     | 440 |     |     |     | 445 |     |     |     |     |

| Ser | Asn | Tyr | Phe | Tyr | Pro | Thr | Tyr | Asp | Glu | Asn | Glu | Glu | Glu | Asn | Arg |
| 450 |     |     |     |     | 455 |     |     |     |     | 460 |     |     |     |     |     |

| Pro | Leu | Met | Arg | Pro | Val | Ser | Glu | Met | Ala | Leu | Leu | Tyr |
| 465 |     |     |     |     | 470 |     |     |     |     | 475 |     |     |

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 2..3
        ( C ) IDENTIFICATION METHOD: Phosphorylated Serine ( i x ) FEATURE:
        ( A ) NAME/KEY: Xaa
        ( B ) LOCATION: 8
        ( C ) IDENTIFICATION METHOD: Phosphorylated Serine ( x i ) SEQUENCE DESCRIPTION: SEQ ID NO:3:

| Met | Xaa | Xaa | Gly | Arg | Arg | Gly | Xaa |
| 1   |     |     |     | 5   |     |     |     |

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 1
        ( C ) IDENTIFICATION METHOD: Phosphorylated Serine ( i x ) FEATURE:
        ( A ) NAME/KEY: Xaa
        ( B ) LOCATION: 3
        ( C ) IDENTIFICATION METHOD: Phosphorylated Serine ( x i ) SEQUENCE DESCRIPTION: SEQ ID NO:4:

```
Xaa Pro Xaa Arg Asp Lys Glu Glu Glu Glu Glu Glu Arg Pro Gly Thr
 1           5                   10                      15
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 5
        ( C ) IDENTIFICATION METHOD: Phosphorylated Serine ( x i ) SEQUENCE DESCRIPTION: SEQ ID NO:5:

```
Ala Pro Gly Arg Xaa Ala Ala
 1           5
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 7
        ( C ) IDENTIFICATION METHOD: Phosphorylated Serine ( x i ) SEQUENCE DESCRIPTION: SEQ ID NO:6:

```
Cys Gln Asn Lys Pro Arg Xaa
 1           5
```

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Xaa
    ( B ) LOCATION: 6
    ( C ) IDENTIFICATION METHOD: Phosphorylated Serine ( x i ) SEQUENCE DESCRIPTION: SEQ ID NO:7:

Glu Leu Leu Lys Tyr Xaa Lys Asp Cys Glu Gly
1               5                   10

( 2 ) INFORMATION FOR SEQ ID NO:8:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 7
        ( C ) IDENTIFICATION METHOD: Phosphorylated Serine ( i x ) FEATURE:
        ( A ) NAME/KEY: Xaa
        ( B ) LOCATION: 11
        ( C ) IDENTIFICATION METHOD: Phosphorylated Serine ( x i ) SEQUENCE DESCRIPTION: SEQ ID NO:8:

Cys Lys Arg Arg Val Glu Xaa Gly Glu Gly Xaa Asp Arg
1               5                   10

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 1
        ( C ) IDENTIFICATION METHOD: Phosphorylated Serine ( x i ) SEQUENCE DESCRIPTION: SEQ ID NO:9:

Xaa Thr Glu Glu Thr Glu Leu Glu His
1               5

( 2 ) INFORMATION FOR SEQ ID NO:10:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 2
        ( C ) IDENTIFICATION METHOD: Phosphorylated Serine ( i x ) FEATURE:
        ( A ) NAME/KEY: Xaa
        ( B ) LOCATION: 4
        ( C ) IDENTIFICATION METHOD: Phosphorylated Serine ( i x ) FEATURE:
        ( A ) NAME/KEY: Xaa ( B ) LOCATION: 8
( C ) IDENTIFICATION METHOD: Phosphorylated Serine ( x i ) SEQUENCE DESCRIPTION: SEQ ID NO:10:

```
Ala  Xaa  Gln  Xaa  Val  Glu  Ile  Xaa  Glu  Glu  Pro  Ala  Glu
1                   5                        10
```

( 2 ) INFORMATION FOR SEQ ID NO:11:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Xaa
      ( B ) LOCATION: 16
      ( C ) IDENTIFICATION METHOD: Phosphorylated Threonine ( x i ) SEQUENCE DESCRIPTION: SEQ ID NO:11:

```
Ser  Pro  Ser  Arg  Asp  Lys  Glu  Glu  Glu  Glu  Glu  Arg  Pro  Gly  Xaa
1                   5                        10                       15
```

( 2 ) INFORMATION FOR SEQ ID NO:12:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Xaa
      ( B ) LOCATION: 5
      ( C ) IDENTIFICATION METHOD: Phosphorylated Threonine ( x i ) SEQUENCE DESCRIPTION: SEQ ID NO:12:

```
Lys  Lys  Gly  Ala  Xaa  Lys  Met  Lys  Asp  Leu  Ala  Arg
1                   5                        10
```

( 2 ) INFORMATION FOR SEQ ID NO:13:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Xaa
      ( B ) LOCATION: 11
      ( C ) IDENTIFICATION METHOD: Phosphorylated Threonine ( x i ) SEQUENCE DESCRIPTION: SEQ ID NO:13:

```
Val  Lys  Lys  Arg  Lys  Gln  Gln  Asp  Gln  Leu  Xaa  Glu  Arg  Asp  Lys  Phe
1                   5                        10                       15
```

( 2 ) INFORMATION FOR SEQ ID NO:14:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
    ( A ) NAME/KEY: Xaa
    ( B ) LOCATION: 5
    ( C ) IDENTIFICATION METHOD: Phosphorylated Threonine ( x i ) SEQUENCE DESCRIPTION: SEQ ID NO:14:

```
Ser  Xaa  Glu  Glu  Xaa  Glu  Leu  Glu  His
1                   5
```

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 5
        ( C ) IDENTIFICATION METHOD: Phosphorylated Tyrosine ( x i ) SEQUENCE DESCRIPTION: SEQ ID NO:15:

```
Glu  Leu  Leu  Lys  Xaa  Ser  Lys  Asp  Cys  Glu  Gly
1                   5                        10
```

( 2 ) INFORMATION FOR SEQ ID NO:16:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 1
        ( C ) IDENTIFICATION METHOD: Phosphorylated Serine ( i x ) FEATURE:
        ( A ) NAME/KEY: Xaa
        ( B ) LOCATION: 3
        ( C ) IDENTIFICATION METHOD: Phosphorylated Serine ( i x ) FEATURE:
        ( A ) NAME/KEY: Xaa
        ( B ) LOCATION: 16
        ( C ) IDENTIFICATION METHOD: Phosphorylated Threonine ( x i ) SEQUENCE DESCRIPTION: SEQ ID NO:16:

```
Xaa  Pro  Xaa  Arg  Asp  Lys  Glu  Glu  Glu  Glu  Glu  Arg  Pro  Gly  Xaa
1                   5                        10                       15
```

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 1
        ( C ) IDENTIFICATION METHOD: Phosphorylated Serine ( i x ) FEATURE:
  ( A ) NAME/KEY: Xaa
  ( B ) LOCATION: 2
  ( C ) IDENTIFICATION METHOD: Phosphorylated Threonine ( i x ) FEATURE:
  ( A ) NAME/KEY: Xaa
  ( B ) LOCATION: 5
  ( C ) IDENTIFICATION METHOD: Phosphorylated Threonine ( x i ) SEQUENCE DESCRIPTION: SEQ ID NO:17:

Xaa  Xaa  Glu  Glu  Xaa  Glu  Leu  Glu  His
1                        5

( 2 ) INFORMATION FOR SEQ ID NO:18:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Xaa
  ( B ) LOCATION: 5
  ( C ) IDENTIFICATION METHOD: Phosphorylated Tyrosine ( i x ) FEATURE:
  ( A ) NAME/KEY: Xaa
  ( B ) LOCATION: 6
  ( C ) IDENTIFICATION METHOD: Phosphorylated Serine ( x i ) SEQUENCE DESCRIPTION: SEQ ID NO:18:

Glu  Leu  Leu  Lys  Xaa  Xaa  Lys  Asp  Cys  Glu  Gly
1                        5                             10

( 2 ) INFORMATION FOR SEQ ID NO:19:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Xaa
  ( B ) LOCATION: 2
  ( C ) IDENTIFICATION METHOD: Phosphorylated Serine ( x i ) SEQUENCE DESCRIPTION: SEQ ID NO:19:

Met  Xaa  Ser  Gly  Arg  Arg  Gly  Ser
1                        5

( 2 ) INFORMATION FOR SEQ ID NO:20:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Xaa
  ( B ) LOCATION: 2..3
  ( C ) IDENTIFICATION METHOD: Phosphorylated Serine ( x i ) SEQUENCE DESCRIPTION: SEQ ID NO:20:

```
Met Xaa Xaa Gly Arg Arg Gly Ser
1               5
```

(2) INFORMATION FOR SEQ ID NO:21:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Xaa
        (B) LOCATION: 3
        (C) IDENTIFICATION METHOD: Phosphorylated Serine (xi) SEQUENCE DESCRIPTION: SEQ ID NO:21:

```
Met Ser Xaa Gly Arg Arg Gly Ser
1               5
```

(2) INFORMATION FOR SEQ ID NO:22:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Xaa
        (B) LOCATION: 3
        (C) IDENTIFICATION METHOD: Phosphorylated Serine (ix) FEATURE:
        (A) NAME/KEY: Xaa
        (B) LOCATION: 8
        (C) IDENTIFICATION METHOD: Phosphorylated Serine (xi) SEQUENCE DESCRIPTION: SEQ ID NO:22:

```
Met Ser Xaa Gly Arg Arg Gly Xaa
1               5
```

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Xaa
        (B) LOCATION: 8
        (C) IDENTIFICATION METHOD: Phosphorylated Serine (xi) SEQUENCE DESCRIPTION: SEQ ID NO:23:

```
Met Ser Ser Gly Arg Arg Gly Xaa
1               5
```

(2) INFORMATION FOR SEQ ID NO:24:

(i) SEQUENCE CHARACTERISTICS:
        (A) LENGTH: 8 amino acids
        (B) TYPE: amino acid
        (C) STRANDEDNESS: single
        (D) TOPOLOGY: linear ( i i ) MOLECULE TYPE: peptide ( i x ) FEATURE:
    ( A ) NAME/KEY: Xaa
    ( B ) LOCATION: 2
    ( C ) IDENTIFICATION METHOD: Phosphorylated Serine ( i x ) FEATURE:
    ( A ) NAME/KEY: Xaa
    ( B ) LOCATION: 8
    ( C ) IDENTIFICATION METHOD: Phosphorylated Serine ( x i ) SEQUENCE DESCRIPTION: SEQ ID NO:24:

```
Met  Xaa  Ser  Gly  Arg  Arg  Gly  Xaa
1                   5
```

( 2 ) INFORMATION FOR SEQ ID NO:25:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 1
        ( C ) IDENTIFICATION METHOD: Phosphorylated Serine ( x i ) SEQUENCE DESCRIPTION: SEQ ID NO:25:

```
Xaa  Pro  Ser  Arg  Asp  Lys  Glu  Glu  Glu  Glu  Glu  Glu  Arg  Pro  Gly  Thr
1                   5                        10                       15
```

( 2 ) INFORMATION FOR SEQ ID NO:26:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 3
        ( C ) IDENTIFICATION METHOD: Phosphorylated Serine ( x i ) SEQUENCE DESCRIPTION: SEQ ID NO:26:

```
Ser  Pro  Xaa  Arg  Asp  Lys  Glu  Glu  Glu  Glu  Glu  Glu  Arg  Pro  Gly  Thr
1                   5                        10                       15
```

( 2 ) INFORMATION FOR SEQ ID NO:27:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 7
        ( C ) IDENTIFICATION METHOD: Phosphorylated Serine ( x i ) SEQUENCE DESCRIPTION: SEQ ID NO:27:

```
Cys  Lys  Arg  Arg  Val  Glu  Xaa  Gly  Glu  Gly  Ser  Asp  Arg
1                   5                        10
```

( 2 ) INFORMATION FOR SEQ ID NO:28:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 7
        ( C ) IDENTIFICATION METHOD: Phosphorylated Serine ( x i ) SEQUENCE DESCRIPTION: SEQ ID NO:28:

```
Cys Lys Arg Arg Val Glu Ser Gly Glu Gly Xaa Asp Arg
 1               5                  10
```

( 2 ) INFORMATION FOR SEQ ID NO:29:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 2
        ( C ) IDENTIFICATION METHOD: Phosphorylated Serine ( x i ) SEQUENCE DESCRIPTION: SEQ ID NO:29:

```
Ala Xaa Gln Ser Val Glu Ile Ser Glu Glu Pro Ala Glu
 1               5                  10
```

( 2 ) INFORMATION FOR SEQ ID NO:30:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 2
        ( C ) IDENTIFICATION METHOD: Phosphorylated Serine ( i x ) FEATURE:
        ( A ) NAME/KEY: Xaa
        ( B ) LOCATION: 4
        ( C ) IDENTIFICATION METHOD: Phosphorylated Serine ( x i ) SEQUENCE DESCRIPTION: SEQ ID NO:30:

```
Ala Xaa Gln Xaa Val Glu Ile Ser Glu Glu Pro Ala Glu
 1               5                  10
```

( 2 ) INFORMATION FOR SEQ ID NO:31:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

( A ) NAME/KEY: Xaa
( B ) LOCATION: 4
( C ) IDENTIFICATION METHOD: Phosphorylated Serine ( x i ) SEQUENCE DESCRIPTION: SEQ ID NO:31:

Ala Ser Gln Xaa Val Glu Ile Ser Glu Glu Pro Ala Glu
1               5                   10

( 2 ) INFORMATION FOR SEQ ID NO:32:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Xaa
( B ) LOCATION: 4
( C ) IDENTIFICATION METHOD: Phosphorylated Serine ( i x ) FEATURE:
( A ) NAME/KEY: Xaa
( B ) LOCATION: 8
( C ) IDENTIFICATION METHOD: Phosphorylated Serine ( x i ) SEQUENCE DESCRIPTION: SEQ ID NO:32:

Ala Ser Gln Xaa Val Glu Ile Xaa Glu Glu Pro Ala Glu
1               5                   10

( 2 ) INFORMATION FOR SEQ ID NO:33:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Xaa
( B ) LOCATION: 8
( C ) IDENTIFICATION METHOD: Phosphorylated Serine ( x i ) SEQUENCE DESCRIPTION: SEQ ID NO:33:

Ala Ser Gln Ser Val Glu Ile Xaa Glu Glu Pro Ala Glu
1               5                   10

( 2 ) INFORMATION FOR SEQ ID NO:34:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Xaa
( B ) LOCATION: 2
( C ) IDENTIFICATION METHOD: Phosphorylated Serine ( i x ) FEATURE:
( A ) NAME/KEY: Xaa
( B ) LOCATION: 8
( C ) IDENTIFICATION METHOD: Phosphorylated Serine ( x i ) SEQUENCE DESCRIPTION: SEQ ID NO:34:

Ala Xaa Gln Ser Val Glu Ile Xaa Glu Glu Pro Ala Glu ( 2 ) INFORMATION FOR SEQ ID NO:35:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 2
        ( C ) IDENTIFICATION METHOD: Phosphorylated Threonine ( x i ) SEQUENCE DESCRIPTION: SEQ ID NO:35:

Ser  Xaa  Glu  Glu  Thr  Glu  Leu  Glu  His
    1                          5

( 2 ) INFORMATION FOR SEQ ID NO:36:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 5
        ( C ) IDENTIFICATION METHOD: Phosphorylated Threonine ( x i ) SEQUENCE DESCRIPTION: SEQ ID NO:36:

Ser  Thr  Glu  Glu  Xaa  Glu  Leu  Glu  His
    1                          5

( 2 ) INFORMATION FOR SEQ ID NO:37:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 1
        ( C ) IDENTIFICATION METHOD: Phosphorylated Serine ( i x ) FEATURE:
        ( A ) NAME/KEY: Xaa
        ( B ) LOCATION: 2
        ( C ) IDENTIFICATION METHOD: Phosphorylated Threonine ( x i ) SEQUENCE DESCRIPTION: SEQ ID NO:37:

Xaa  Xaa  Glu  Glu  Thr  Glu  Leu  Glu  His
    1                          5

( 2 ) INFORMATION FOR SEQ ID NO:38:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide -continued

```
( i x ) FEATURE:
       ( A ) NAME/KEY: Xaa
       ( B ) LOCATION: 1
       ( C ) IDENTIFICATION METHOD: Phosphorylated Serine ( i x ) FEATURE:
       ( A ) NAME/KEY: Xaa
       ( B ) LOCATION: 5
       ( C ) IDENTIFICATION METHOD: Phosphorylated Threonine ( x i ) SEQUENCE DESCRIPTION: SEQ ID NO:38:

Xaa Thr Glu Glu Xaa Glu Leu Glu His
 1               5
```

IMMUNOGENIC CANCER PROTEINS AND PEPTIDES AND METHODS OF USE

CROSS-REFERENCE TO RELATED APPLICATION

This application is a Continuation-In-Part application of U.S. patent application Ser. No. 08/049,698, filed Apr. 16, 1993 now abandoned, the disclosure of which is incorporated herein by reference.

DESCRIPTION

1. Technical Field of the Invention

The field of this invention is tumor-specific antigens, proteins or peptides that are selectively immunogenic for tumor patients. These immunogenic proteins or peptides can be identified by the presence of antibodies specific for those proteins and/or peptides in tumor patient sera. This invention also relates to a process for identifying and isolating, from other tumors, intracellular proteins and/or peptides which are selectively immunogenic for patients afflicted with those tumors. This invention also relates to a method of predicting, in individual tumor patients, which proteins or peptides would be most useful in generating effector T cells for adoptive immunotherapy or for formulating specific vaccines.

2. Background of the Invention

Methods for isolating and expanding human T lymphocyte reactive to and having a positive therapeutic effect upon autologous tumor have been described in tumor immunology. See Greenberg et. al, Adoptive T Cell Therapy of Tumors: Mechanism Operative in the Recognition and Elimination of Tumor Cells, ADV. in Immunol. V.49, 281 (Academic Press, Inc. 1991). Greenberg and Cheever describe the evolutionary development of adoptive T cell therapy in a murine tumor model and parallel, yet still early, development of a similar capability for human tumors. Initial studies involving the murine model, a Friend virus induced erythroleukemia (FBL), illustrated that disseminated antigenic tumors could be eradicated by the adoptive transfer of T cells specifically reactive to the tumor. Cheever, M. A., et al., *J. Immunol.* 126:1318–1322 (1981); Cheever, M. A., et al., *J. Biol. Response Mod.* 3(5):462–7 (1984); Cheever, M. A., et al., *J. Biol. Response Mod.* 3(2):113–27 (1984); Cheever, M. A., et al., *Immunol.* 132(5):2259–65 (1984); Cheever, M. A., et al., *J. Immunol.* 134(6):3895–900 (1985); Cheever, M. A., et al., *Prog. Clin. Biol. Res.* 244:49–58 (1987); Cheever, M. A., et al., *J. Exp. Med.* 163(5):110–12 (1986); Cheever, M. A., et al. *Immunobiology* 172(3–5):365–82 (1986); Chen, W., et al., *J. Immunol.* 144(10):3659–66 (1990); Chen, W., et al., *Proc. Natl. Acad. Sci USA* 89(4):1468–72 (1992); Crossland, K. D., et al., *J. Immunol.* 146(12):4414–20 (1991); Greenberg, P. D., et al., *J. Immunol.* 123(2):515–22 (1979); Greenberg, P. D., et al., *J. Exp. Med.* 154(3):952–63 (1981); Greenberg, P. D., et al., *J. Immunol.* 126:2100–2103 (1981); Greenberg, P. D., et al., *J. Biol. Response Mod.* 3(5):455–61 (1984); Greenberg, P. D., et al. *J. Immunol.* 133(6):3401–7 (1984); Greenberg, P. D., et al., *Surv. Immunol. Res.* 40:283–96 (1985); Greenberg, P. D., et al., *J. Exp. Med* 161(5):1122–34 (1985); Greenberg, P. D., et al., *Prog. Clin. Biol. Res.* 244:127–35 (1987); Greenberg, P., et al., *Symp. Princess Takamatsu Cancer Res. Fund* 19:287–301 (1988); Greenberg, P. D., et al., *Prog. Exp. Tumor Res.* 32:104–27 (1988); Greenberg, P., et al., *Int. Symp. Princess Takamatsu Cancer Res. Fund* 19:287–301 (1988); Kern, D. E., et al., *J. Immunol.* 136(11):4303–10 (1986); Kern, D. E., et al., *J. Immunol.* 141(8):2824–30 (1988); Kern, D. E., et al., *Cancer Res.* 50(19):6256–63 (1990); Klarnet, J. P., et al., *J. Immunol.* 138:4012–4017 (1987); Klarnet, J. P., et al., *J. Immunol.* 142(7):2187–91 (1989); Klarnet, J. P., et al., *J. Exp. Med.* 169(2):457–67 (1989); Peace, D. J., et al. *J. Exp. Med.* 169(1):161–73 (1989). Later studies illustrated that the limited therapeutic activity of small numbers of tumor-reactive T cells could be greatly augmented by growing the T cells to large numbers in-vitro and treating with the large numbers of cells (Cheever, M. A., et al., *Prog. Clin. Biol. Res.* 244:49–58 (1987); Cheever, M. A., et al., *J. Exp. Med.* 163(5):110–12 (1986); Klarnet, J. P., et al., *J. Immunol.* 138:4012–4017 (1987)). Furthermore, a great deal of successful study defined the requirements for generating CD4+ and CD8+ anti-tumor effector cells as the individual requirements were quite different for the two cell types. Up to the present time, various investigators have shown that human effector T cells specific for autologous tumor can be isolated and expanded in-vitro (Ioannides, C. G., et al., *J. Immunol.* 146(5):1700–7 (1991); Mukherji, B., et al., *Immunol. Rev.* 116:33–62 (1990); Viale, M., et al., *Tumori* 76(5):488–94 (1990)). However significant limitations still exist in being able to apply all of the lessons learned from the FBL model to human work. The major barriers to overcome are: (1) identifying tumor protein antigens both synthesized by malignant cells and recognizable by patient T cells (immunogenic proteins) with minimal or no recognition by control subject T cells; (2) possessing enough immunogenic proteins (a library of potential immunogenic proteins) as to provide sufficient immunogenic recognition of most cells which constitute an individual tumor type as each patient's tumor is composed of individual cell sub-types which may or may not be synthesizing any one give protein antigen; (3) determining which antigens contained in the library of immunogenic proteins are actually being synthesized by each patients' tumor; and (4) determining which protein or peptide antigens in the library of immunogenic proteins are presentable by the MHC molecules possessed by the individual patient and are therefore immunogenic for that patient as not all patients' T cells can respond equally to any given protein antigen or its constituent peptide epitopes because of MHC restriction. To date, a highly specific humoral and/or cellular immune response directed against common tumors has been reported for only a few antigens. Documented examples of a humoral response directed against tumors are those of Davidoff, A. M., Iglehart, J. D., Marks, J. R., *Social Sciences* 89:3439–3442 (1992) describing a human serum antibody response to the p53 protein over-expressed by breast cancer cells and that of Ben-Maharez, K., Thierry, D., Sorokine, Danna-Muller, A., Kohiyama, M., *Br. J. Cancer* 57:529–534 (1988), and others describing circulating antibodies to c-myb and c-myc proteins in patients with breast and colorectal cancers. In the case of Davidoff, age and gender-matched control sera were not tested thereby preventing a determination of immunogenic specificity for tumor patients versus normal subjects. In the case of Ben-Maharez, Soroidne and others, there was an absence of absolute qualitative immunogenic specificity shown between tumor patients and normal subjects. The quantitative specificity was also too low to be diagnostically or therapeutically useful. Documented examples of a cellular immune response directed against human tumor antigens are those of Finn describing the core protein of epithelial mucin and van der Bruggen, P., Traversari, C., Chomez, P., Lurquin, C., De Plaen, E., van den Eynde, B., Knuth, A., Boon, T., *Science* 254:1643–1647 (1991) describing the MAGE antigen of melanoma, breast cancer and other tumors. The epithelial mucin is an intracellular antigen in normal epithelial cells and an intracellular and extracellular antigen in some tumor cells. The cellular localization of the MAGE antigen was not described and it too was not synthesized by all melanoma or breast cancer cell lines. The cellular immune response described in each case was a cytotoxic T lymphocyte (CTL) response. While the CTL response of mucin was not MHC restricted, the CTL response to MAGE was restricted only to the HLA-A1 haplotype. The utility of MAGE or mucin in generating a humoral immune response was not tested.

BRIEF SUMMARY OF THE INVENTION

In one aspect, the present invention provides a tumor specific antigen prepared by a process comprising the steps of: (a) identifying a selectively immunogenic protein present in a tumor cell; and (b) isolating and purifying the protein. Identifying preferably comprises screening control and tumor patient sera to determine which protein specifically immunoreacts with an antibody in tumor patient sera. The antibody can be an IgA, IgE, IgG or IgM immunoglobulin.

The present invention also contemplates a tumor specific antigen preparable by such a process. In one preferred embodiment, a tumor specific antigen is a SCC (squamous cell carcinom) antigen such as SCC antigen 3.3, 16.1, 16.3, 16.4, 27.3, 35.1, 37.1, 37.2, 39.1, 39.2, 39.4, 40.1, 40.3, 40.4, 47.2, 47.3, 47.4, 49.2, 49.3, 50.1, 50.2 or 50.3.

In another preferred embodiment, a tumor specific antigen is a breast cancer specific antigen such as phosphorylated dbl, which dbl preferably comprises the amino acid residue sequence of SEQ ID NO:2. Phosphorylated dbl comprises, in various embodiments, one or more phosphorylated serine, threonine or tyrosine residues. Where phosphorylated dbl comprises at least one phosphorylated serine residue, that residue is preferably located at amino acid residue position number 2, 3, 9, 23, 25, 47, 151, 202, 295, 299, 402, 436, 438, or 442 of SEQ ID NO:2. Where phosphorylated dbl comprises at least two phosphorylated serine residues, those residues are preferably located at amino acid residue position numbers 2 and 3, 2 and 9, 3 and 9, 23 and 25, 295 and 299, 436 and 438, 436 and 442, or 438 and 442 of SEQ ID NO:2. Where phosphorylated dbl comprises at least three phosphorylated serine residues, those residues are preferably located at amino acid residue position numbers 2, 3 and 9 or 436, 438 and 442 of SEQ ID NO:2.

Where phosphorylated dbl comprises at least one phosphorylated threonine residue, that residue is preferably located at amino acid residue position number 38, 263, 380, 403 or 406 of SEQ ID NO:2. Where phosphorylated dbl comprises at least two phosphorylated threonine residues, those residues are preferably located at amino acid residue position numbers 403 and 406 of SEQ ID NO:2.

Where phosphorylated dbl comprises at least one phosphorylated tyrosine residue, that residue is preferably located at amino acid residue position number 201 of SEQ ID NO:2.

Phosphorylated dbl can also comprise more than one type of phosphorylated amino acid residue. In one embodiment, phosphorylated dbl comprises at least one phosphorylated serine residue and at least one phosphorylated threonine residue, preferably wherein a) two phosphorylated serine residues are located at amino acid residue position numbers 23 and 25 of SEQ ID NO:2 and one phosphorylated threonine residue is located at amino acid residue position number 38; b) one phosphorylated serine residue is located at amino acid residue position number 402 of SEQ ID NO:2 and two phosphorylated threonine residues are located at amino acid residue position numbers 403 and 406 of SEQ ID NO:2; or c) one phosphorylated serine residue is located at amino acid residue position number 402 of SEQ ID NO:2 and one phosphorylated threonine residue is located at amino acid residue position number 403 or 406 of SEQ ID NO:2.

Where phosphorylated dbl comprises at least one phosphorylated serine residue and at least one phosphorylated tyrosine residue, those residues are preferably situated wherein one phosphorylated serine residue is located at amino acid residue position number 202 of SEQ ID NO:2 and one phosphorylated tyrosine residue is located at amino acid residue position number 201 of SEQ ID NO:2. In another embodiment, phosphorylated dbl comprises the amino acid residue sequence of SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38.

In another aspect, the present invention provides a process of identifying a functional protein of a tumor cell comprising identifying a protein present in the tumor cell that is selectively immunogenic for tumor patients. In one embodiment, the tumor cell is a SCC cell or a breast cancer cell. In a preferred embodiment, the functional protein is selectively functional for the tumor cell.

In another aspect, the present invention provides a process of making a functional protein of a tumor cell comprising the steps of (a) identifying a protein present in the tumor cell, which protein is selectively immunogenic for tumor patients; and (b) isolating and purifying the protein. The present invention also contemplates a protein made by that process. In another embodiment, a process of making a functional protein of a tumor cell further comprises the steps of (c) sequencing the isolated and purified protein; (d) preparing a polynucleotide that encodes the sequenced protein; (e) transfecting a host cell with an expression vector comprising the polynucleotide; (f) maintaining the transfected host cell under conditions sufficient for expression of the protein; and (g) collecting the protein.

In yet another aspect, the present invention provides a process of increasing the immunogenic specificity of a tumor-associated antigen comprising phosphorylating the tumor-associated antigen. Preferably the tumor antigen is a breast cancer antigen such as dbl that comprises the amino acid residue sequence of SEQ ID NO:2.

In another aspect, the present invention provides an assay kit for detecting the presence of an antibody immunoreactive with a tumor-specific antigen comprising in an amount sufficient for at least one assay a tumor-specific antigen. The tumor specific antigen is preferably SCC antigen 3.3, 16.1, 16.3, 16.4, 27.3, 35.1, 37.1, 37.2, 39.1, 39.2, 39.4, 40.1, 40.3, 40.4, 47.2, 47.3, 47.4, 49.2, 49.3, 50.1, 50.2 or 50.3 or phosphorylated dbl. The kit can further comprise means for detecting the antibody immunoreacted with the tumor-specific antigen. The antibody is an IgA, IgE, IgG or IgM immunoglobulin.

In still yet another aspect, the present invention provides a process of detecting the presence in a biological fluid of an antibody immunoreactive with a tumor-specific antigen, the process comprising the steps of: (a) forming an admixture with a sample of the body fluid and the tumor-specific antigen; (b) maintaining the admixture under biological reaction conditions for a period of time sufficient for formation of a conjugate between antibody present in the sample and the tumor-specific antigen; and (c) detecting the presence of the conjugate. The tumor specific antigen is preferably SCC antigen 3.3, 16.1, 16.3, 16.4, 27.3, 35.1, 37.1, 37.2, 39.1, 39.2, 39.4, 40.1, 40.3, 40.4, 47.2, 47.3, 47.4, 49.2, 49.3, 50.1, 50.2, 50.3 or phosphorylated dbl. The antibody is an IgA, IgE, IgG or IgM immunoglobulin.

The present invention still further provides a process of making T cells sensitized to a tumor-specific antigen, the process comprising the steps of: (a) isolating a population of autologous T cells containing virgin non-antigen sensitized T cells; (b) identifying an immunogenic tumor-specific antigen; and (c) sensitizing the non-antigen sensitized T cells with the immunogenic tumor-specific antigen. The tumor specific antigen is preferably SCC antigen 3.3, 16.1, 16.3, 16.4, 27.3, 35.1, 37.1, 37.2, 39.1, 39.2, 39.4, 40.1, 40.3, 40.4, 47.2, 47.3, 47.4, 49.2, 49.3, 50.1, 50.2, 50.3 or phosphorylated dbl. The T cells are preferably T-helper lymphocytes or specific cytotoxic T cells.

In another embodiment, a process of preparing a population of T cells sensitized to a tumor-specific antigen comprises the steps of: (a) isolating T cells sensitized to the tumor-specific antigen; and (b) inducing numerical expansion of the sensitized T cells. Inducing is preferably accomplished in the presence of the tumor-specific antigen and, if necessary, antigen presenting cells. The T cells used in this process are preferably isolated from circulating lymphocytes, lymph nodes or tumors. This process can further comprise the steps of: (c) sub-culturing the T cells to identify T cells sensitized to a particular tumor-specific epitope. The immunogenic tumor specific antigen is preferably SCC antigen 3.3, 16.1, 16.3, 16.4, 27.3, 35.1, 37.1, 37.2, 39.1, 39.2, 39.4, 40.1, 40.3, 40.4, 47.2, 47.3, 47.4, 49.2, 49.3, 50.1, 50.2, 50.3 or phosphorylated dbl.

The present invention still further provides a process of making a peptide library of tumor specific humoral antigens. That process comprises the steps of: (a) isolating one or more selectively immunogenic proteins from tumor cells; (b) identifying in each of the selectively immunogenic proteins one or more epitopes that are selectively immunogenic for tumor patients; (c) preparing for each epitope a peptide that contains the epitope, wherein no single peptide contains an epitope recognized by non-tumor subjects; and (d) forming a library of the peptides. In one embodiment, isolating comprises the steps of: (a) extracting proteins from a tumor cell; (b) screening control and tumor patient sera to determine which of the proteins specifically immunoreact with an antibody in tumor patient sera; and (c) isolating and purifying the selectively immunogenic protein. Identifying preferably comprises the steps of: (a) defining potential epitopes in the protein; (b) synthesizing peptides comprising a portion of the protein, which portion contains one of the epitopes; and (c) screening control and tumor patient sera to determine which of the proteins specifically immunoreact with an antibody in tumor patient sera and thus identifying epitopes in the protein that are selectively immunogenic for tumor patients. The selectively immunogenic protein can be a phosphorylated protein. The present invention also contemplates a library prepared by this process.

In another aspect, the present invention further provides a process of making a peptide library of breast cancer specific humoral antigens comprising the steps of: (a) identifying proteins present in breast cancer cells that are selectively immunogenic for breast cancer patients; (b) defining potential phosphorylation sites of the proteins; (c) synthesizing peptides comprising a portion of the protein, which portion contains at least one of the phosphorylation sites and wherein at least one of the phosphorylation sites is phosphorylated; (d) screening the peptides to identify phosphorylated peptides that are selectively immunogenic for breast cancer patients; and (e) forming a library of the phosphorylated selectively immunogenic peptides. In one embodiment of that process, the protein is dbl and the potential phosphorylation sites comprise: (a) a phosphorylated serine residue at amino acid residue position number 2, 3, 9, 23, 25, 47, 151, 202, 295, 299, 402, 436, 438, or 442 of SEQ ID NO:2; (b) at least two phosphorylated serine residues located at amino acid residue position numbers 2 and 3, 2 and 9, 3 and 9, 23 and 25, 295 and 299, 436 and 438, 436 and 442, or 438 and 442 of SEQ ID NO:2; (c) at least three phosphorylated serine residues located at amino acid residue position numbers 2, 3 and 9 or 436, 438 and 442 of SEQ ID NO:2; (d) a phosphorylated threonine residue located at amino acid residue position number 38, 263, 380, 403 or 406 of SEQ ID NO:2; (e) at least two phosphorylated threonine residues located at amino acid residue position numbers 403 and 406 of SEQ ID NO:2; (f) at least one phosphorylated tyrosine residue located at amino acid residue position number 201 of SEQ ID NO:2; (g) at least one phosphorylated serine residue and at least one phosphorylated threonine residue wherein (i) the phosphorylated serine residue is located at amino acid residue position numbers 23 and 25 of SEQ ID NO:2 and one phosphorylated threonine residue is located at amino acid residue position number 38;

(ii) one phosphorylated serine residue is located at amino acid residue position number 402 of SEQ ID NO:2 and two phosphorylated threonine residues are located at amino acid residue position numbers 403 and 406 of SEQ ID NO:2; or (iii) one phosphorylated serine residue is located at amino acid residue position number 402 of SEQ ID NO:2 and one phosphorylated threonine residue is located at amino acid residue position number 403 or 406 of SEQ ID NO:2; or (h) at least one phosphorylated serine residue and at least one phosphorylated tyrosine residue wherein the phosphorylated serine residue is located at amino acid residue position number 202 of SEQ ID NO:2 and the phosphorylated tyrosine residue is located at amino acid residue position number 201 of SEQ ID NO:2. The protein portion in the above process preferably comprises the amino acid residue sequence of SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38. In a preferred embodiment, the protein is an oncogene-transcribed protein, a cell-cycle protein, a receptor, a transcription factor or other regulatory protein or substrate protein or. The present invention also contemplates a library prepared by this process.

In a still further aspect, the present invention provides an assay kit for diagnosing the presence of a tumor in a subject, the kit comprising in an amount sufficient for at least one assay a peptide library of tumor specific humoral antigens. Where the tumor is SCC, the library preferably comprises two or more of SCC antigens 3.3, 16.1, 16.3, 16.4, 27.3, 35.1, 37.1, 37.2, 39.1, 39.2, 39.4, 40.1, 40.3, 40.4, 47.2, 47.3, 47.4, 49.2, 49.3, 50.1, 50.2 or 50.3. Where the tumor is breast cancer, the library preferably comprises a plurality of two more of peptides designated SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38.

Figure 1:
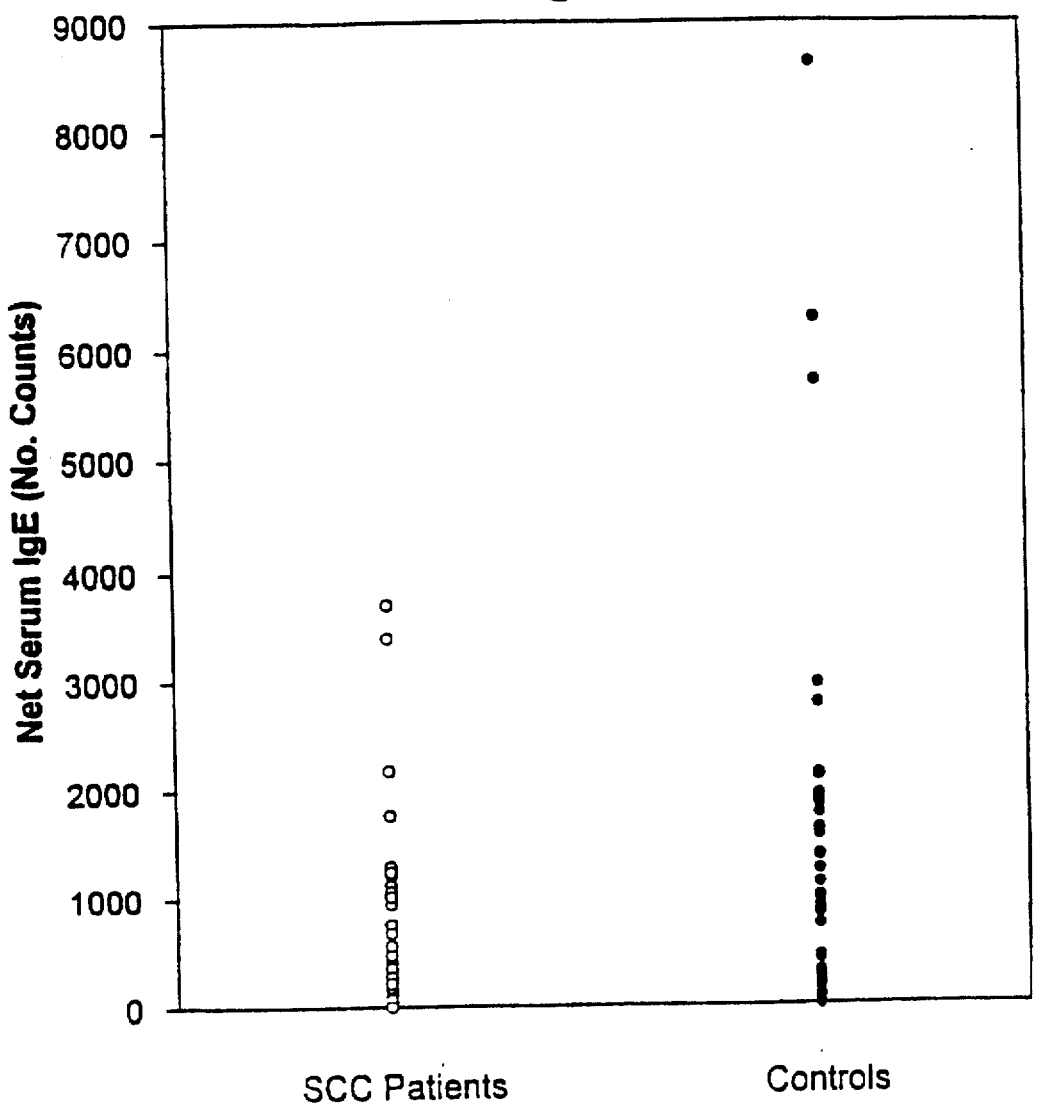
FIG. 1 shows distribution of squamous cell carcinoma (SCC) intracellular protein-specific IgE values for 31/65 head and neck carcinoma patients (SCC Pts), and 40/65 control subjects (Controls). The source antigen employed in this assay system was a mixture of all intracellular protein extracted from the SCC cells.

FIG. 2 shows that Patients exhibited a higher prevalence of serum IgA binding to SCC intracellular proteins (17/65) than did age and gender matched controls (1/65). Plot illustrates distribution of SCC intracellular protein-specific IgA values for head and neck carcinoma patients (SCC Pts) and control subject (Controls). The source antigen was as for FIG. 1.

FIG. 3A shows a plot of individual patient serum IgE versus IgA. More specifically this figure shows an inverse relationship exists between the ability of SCC patients to produce IgE and their ability to produce IgA and/or IgG in response to immune stimulation with SCC intracellular proteins. The source antigen was as for FIG. 1.

FIG. 3B shows a plot of individual patient serum IgE versus IgG. The source of antigen was as for FIG. 1.

Figure 4:
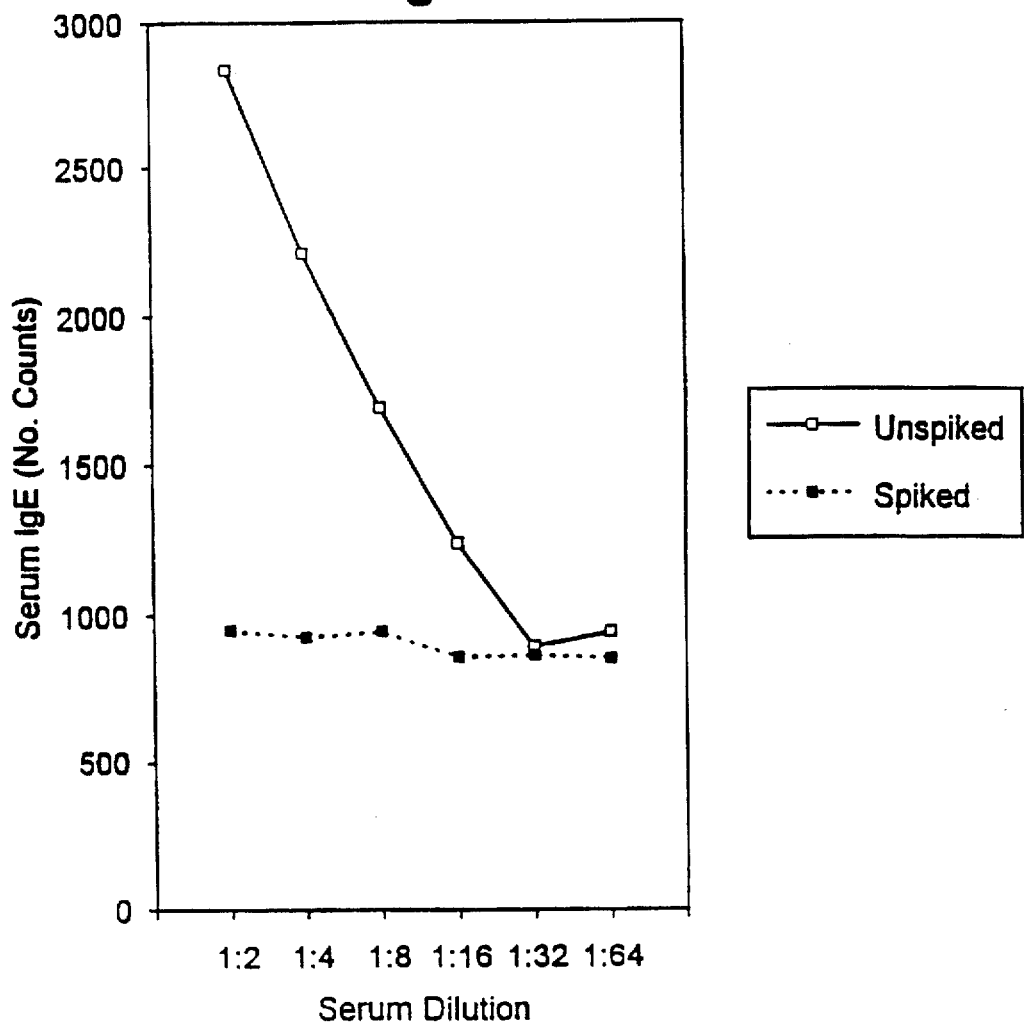

FIG. 4 shows Specificity of serum immunoglobulin binding to SCC cytoplasmic proteins was confirmed by isotype-specific antigen-inhibition studies. Ten random immunoglobulin-positive sera were used for each isotype category. IgE-positive sera were diluted 1:2 with 8% human serum albumin. IgA and IgG-positive sera were diluted 1:2 with neat goat serum. An aliquot corresponding to each dilution was spiked with 2.5 mg/mL of SCC intracellular proteins. The immunoglobulin signal for all sera tested was inhibited by spiking with specific antigen. Plot illustrates total elimination of specific IgE signal for antigen-spiked dilutions (solid square) as compared to unspiked dilutions (empty square) in one patient sample.

FIG. 5A shows highly specific tumor antigens (HSTA) were identified by western blot analysis of SCC cytoplasmic protein fractions. The IgA binding profiles of twenty-four HSTA tested against fourteen SCC patient and ten age and gender matched control sera are illustrated.

FIG. 5B shows highly specific tumor antigens (HSTA) were identified by western blot analysis of SCC cytoplasmic protein fractions. The IgA binding profiles of twenty-four HSTA tested against fourteen SCC patient and ten age and gender matched control sera are illustrated.

FIG. 6 shows p66 dbl humoral immunogenicity. Sera from breast cancer patients with Stage I and II disease were tested for IgA reactivity along with sera for age-matched female subjects with benign breast lesions.

FIG. 7 shows p66 dbl IgG-reactivity with breast cancer patient sera than with control sera. The quantification of reactivity between dbl and IgA+IgG was also more significant for breast cancer patient sera than for control sera.

FIG. 8 shows breast cancer-specific IgA reactivity using phosphorylated p66 dbl (2+3) as compared to the non-phosphorylated version (FT). Antigen inhibition studies using FT dbl as the spiking antigen and 2+3 as the blotting antigen resulted in absolute specificity for the cancer patients sera.

FIG. 9 shows sensitivity and specificity of large numbers of breast cancer patient sera and control sera with the inhibition-type p66 dbl assay. Assay sensitivity appeared good at all breast cancer stages.

Figure 10:
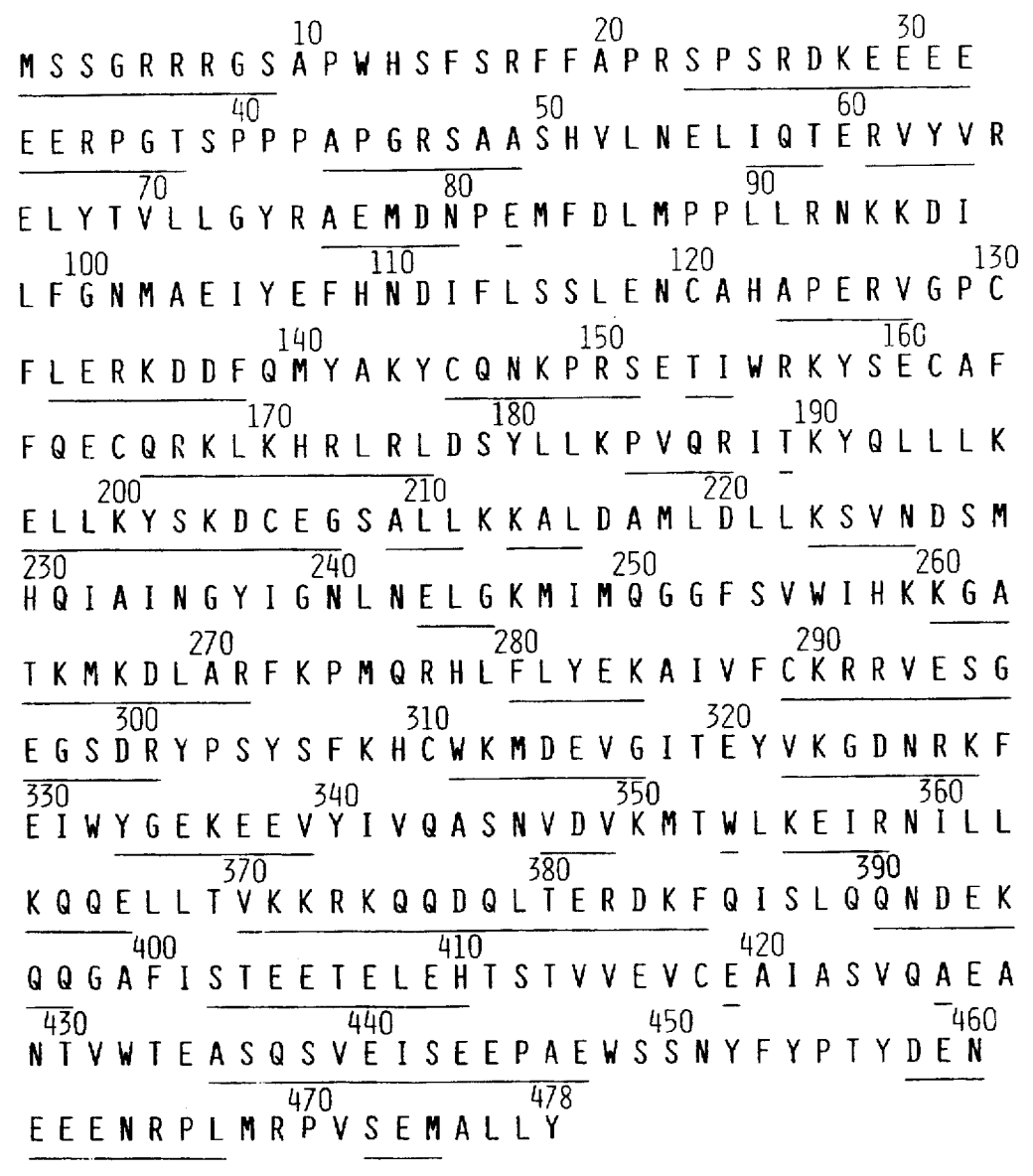

FIG. 10 shows a rolling sum analysis of the amino acid sequence of p66 dbl with potentially phosphorylateable serine, threonine or tyrosine residues. Surface peptide sequences are underlined. Potentially phosphorylateable residues are highlighted in bold.

FIG. 11 shows many intracellular proteins and receptor proteins possessing intracellular portions undergo phosphorylation. A partial list of 210 molecules is provided.

DETAILED DESCRIPTION OF THE INVENTION

The Invention

To date, the identification and isolation of tumor-associated proteins has been accomplished only through the use of four or five laborious procedures: transfection analysis; oncogene product complex formation; DNA/RNA probe hybridization; monoclonal antibody production and screening; and DNA library creation and screening.

In accordance with transfection analysis, fibroblasts (e.g., 3T3 fibroblasts) are transfected with DNA isolated and purified from tumor cells. Those transfected fibroblasts (primarily transfectants) are transformed by transforming genes (e.g., oncogenes) in the tumor cell DNA. The DNA from the primary transfectants can then be used to create second and third-cycle transfectants also transformed by transforming DNA. The DNA/RNA is isolated from the transformed cells and those nucleic acids responsible for transformation identified. Those transforming nucleic acids are then sequenced and the encoded tumor-associated proteins identified.

Transfection analysis has been used to identify B-cell lymphoma oncogenes (Eva & Aaronson, Isolation of a new human oncogene from a diffuse B-cell lymphoma, Nature, 1985;316:273–275); transforming genes from chemically transformed cells (Cooper et al., Molecular cloning of a new transforming gene from a chemically transformed human cell line, Nature, 1984;311:29–33); malignant melanomas (Padua et al., A novel transforming gene in a human malignant melanoma cell line, Nature, 1984;311:671–673), lymphomas (Takahashi et al., Activation of a Novel Human Transforming Gene, ret, by DNA Rearrangement, Cell, 1985,42:581–588), mammary carcinomas (Fasano et al., New Human Transforming Gene Detected by a Tumorigenicity Assay, Molecular and Cellular Biology, 1984,4(9):1695–1705); and a variety of other oncogenes (Cooper and Lane, Cellular Transforming Genes and Oncogenesis. Biochimica et Biophysica Acta, 1984,738:9–20; Schechter et al., The neu oncogene: an erb-B-related gene encoding a 185,000-$M_r$ tumour antigen, Nature, 1984,312:513–516; Martin-Zanca, A human oncogene formed by the fusion of truncated tropomyosin and protein tyrosine kinase sequences, Nature, 1986,319:743–748; Shimizu et al., Molecular cloning of an activated human oncogene, homologous to v-raf, from primary stomach cancer, Proc. Natl. Acad. Sci. USA, 1985, 82:5641–5645; Land et al., Cellular Oncogenes and Multi-step Carcinogenesis, Science, 1983,222:771778).

Tumor-associated proteins can also be identified through a process of determining which proteins in tumor cells coprecipitate with known tumor cell proteins in immune complexes. This procedure has been used to identify two phosphorylated proteins associated with Rous sarcoma virus transformed cells (Oppermann et al., Two Cellular Proteins that Immunoprecipitate with the Transforming Protein of Rous Sarcoma Virus, Virology, 1981,113:736–751).

In a third established procedure, tumor-associated proteins are identified through the use of DNA/RNA hybridization probes. A labelled (e.g., $^{32}P$) DNA or RNA molecule known to be associated with a transforming virus (e.g., a retrovirus) is prepared. That labelled polynucleotide is then exposed to DNA/RNA from a normal or transformed cell. Hybridized polynucleotides are identified and sequenced. This procedure has been used to identify a vertebrate homology of the putative transforming gene of avian myelocytomatosis virus (Sheiness et al., The Vertebrate Homolog of the Putative Transforming Gene of Avian Myelocytomatosis Virus: Characteristics of the DNA Locus and Its RNA Transcript, *Virology*, 1980,105:415–424), an RNA molecule related to an Avian sarcoma virus transforming gene (Spector et al., Uninfected Avian Cells Contain RNA Related to the Transforming Gene of Avian Sarcoma Viruses. *Cell*, 1978.13:371–379) and v-raf (Rapp et al., Structure and biological activity of v-raf, a unique oncogene transduced by a retrovirus. *Proc. Natl. Acad. Sci. USA*, 1983,80:4218–4222). Polynucleotide probes have also been used to screen DNA libraries (Quintrell et al., Identification of a Human Gene (HCK) That Encodes a Protein-Tyrosine Kinase and Is Expressed in Hemopoietic Cells, *Molecular and Cellular Biology*, 1987.7(6):2267–2275).

Monoclonal antibodies have also been used to identify tumor-associated proteins. In accordance with that procedure, tumor cells are disrupted to produce a composition containing tumor cell proteins. Mice are immunized with that composition. Spleen cells are collected and isolated from the immunized mice and fused with myeloma cells to create immortalized hybridoma cell line that produce and secrete individual monoclonal antibodies against a particular antigen. Those monoclonal antibodies are than used to screen populations of putative tumor cell antigens, which antigens immunoreact with one or more of the antibodies. Tumor cell antigens identified in the manner can then be purified and characterized (e.g., sequenced). Monoclonal antibodies have been used to characterize sarcoma-associated antigen p102 (Brown et al., Monoclonal Antibody Characterization of Sarcoma—Associated Antigen p102, *Anticancer Research*, 1991,11:1565–1570).

In contrast to the above procedures using numerous and often laborious steps, the present invention provides a simple procedure for identifying tumor specific antigens, which procedure relies upon the production of antisera against such antigens by tumor subjects/patients. In particular, the present application relates to tumor specific antigens, proteins or peptides that provoke a humoral immune response in sera from tumor patients. For purposes of clarity of disclosure, and not by way of limitation, the detailed description of the invention is divided into the following subsections:

(A) A process of identifying/making tumor specific antigens and tumor specific antigens made by that process.

(B) A process of identifying/making functional proteins of tumor cells and functional proteins by that process.

(C) Kits and processes for detecting antibodies to tumor specific antigens.

(D) A process of making/preparing populations of T cells sensitized to tumor specific antigens.

(E) A process of increasing the immunospecificity of tumor associated proteins.

(F) A process of making a peptide library of tumor specific antigens.

(G) A kit for detecting the presence of a tumor cell in a subject.

A. Tumor-specific humoral antigens

In one aspect, the present invention provides a tumor specific antigen preparable by, and preferably prepared by, a process comprising the steps of: (a) identifying a selectively immunogenic protein present in a tumor cell; and (b) isolating and purifying the protein. Identifying preferably comprises screening control and tumor patient sera to determine which protein specifically immunoreacts with an antibody in tumor patient sera. The antibody can be an IgA, IgE, IgG or IgM immunoglobulin.

The term antigen includes antigenic fragments, whether derived from patient tumor samples or synthetically or recombinantly produced. Antigen proteins having substantial homology to antigen or fragments thereof can also be used in accordance with the invention. Additionally, antigen analogs are also contemplated. The term tumor includes: carcinoma, sarcoma, myeloid malignancies, lymphoid malignancies, and neurogenic malignancies. Thus, the term tumor-specific antigen includes substantially pure compositions capable of inducing MHC restricted T cell response. These tumor antigens differ from protein and peptides found in normals in that they are selectively immunogenic. These proteins or polypeptides are selectively immunogenic because they are specifically expressed in tumor cells, expressed in abnormally high quantities in tumor cells and/or they are immunologically exposed in tumor cells whereas in normal cells they are shielded from the immune system.

Tumor antigens can include proteins or polypeptides, or fragments thereof. Tumor antigens are preferably derived from the following groups:

Cytoplasmic Proteins Associated with Cell Growth and Differentiation p145 abl, p105 akf, p22 arf, p160 bcr, p33 cdc2, p34 cdc2, p25 cdc42, p25 cdc 42 GAP, p66 dbl , p45 ERK 4, p54 MAPK, p42 MAPK 1(ERK 2), p44 MAPK 2(ERK 1), p39 pim, p21 rab1, p21 rab2, p25 rab3A, p74 raf, p68 raf-1, p74 raf-1, p21 ras (inactive), p120 ras GAP, p295 ras GAP, p35 ras exchange protein, p160 ras exchange protein, p100–160 ras exchange protein, p53.

Inner Membrane Surface Attached Molecule src gene family—p60 src, p62 yes, p60 yrk, p56 lck, p60 fgr, p57 Hck, p59 fyn, p58 lyn and p55 blk; abl gene family—p145 abl and p145 arg; and Fps gene family—p93 fes.

Inner Membrane-Portion of Membrane Growth Factor Receptors

Nerve growth factor receptor family: p140 trk, p145 trkB and p145 trkC, Hepatocyte growth factor p195 met, Epidermal growth factor Receptor Family—p185 erb $B_2$, p160 erb $B_3$ and p170 erb $B_1$ (EGF-R) and Fibroblast Growth Factor Receptor Family p150 FGF-R1/flg, p105 FGF-R2/bek, p125 FGF-R3, and p140 FGF-R4.

p32-src Receptor

Regulatory Proteins of DNA Synthesis p42 cyclin C, p34 cyclin D, p33 cdk2, p60 cyclin A, p45 cyclin E, p34 cdc 2, p33 mos, p62 cyclin B1/B2, and p34 cyclic D/PRAD 1/bcl-1.

DNA Binding and Gene Expression Proteins p62 fos, p62 fos B, p46 fra 1, p39 jun, p39 jun B, NF-κB, rhoB and p17 max.

Nuclear Oncogenes and Transcription Factors p50 ets-1, p53 ets-2, p75 ski, p72 sno, p145 evi-1, p135 cbl, p80 rel, p43 CREB, p39 c-jun, p98 lyt, p52 erb A alpha, p52 erb A beta, p88 glucocorticoid receptor, p66 estrogen-R, p145 abl, and p145 arg.

Other proteins or fragments thereof not yet known having the characteristics of highly specific tumor antigens are also contemplated by the present invention. Some tumor-derived proteins are significantly present in tumor cells and are absent from or present in very low amounts in normal cells. These, therefore, present as highly specific targets of an anti-tumor humoral and cellular immune response and are therefore named highly specific tumor antigens (HSTA). More specifically, the term highly specific tumor antigen means a substantially pure composition capable of inducing MHC restricted T cell response.

Proteins can be isolated from tumor cells using standard procedures well known in the art. By way of example, a three step separation method is used. First, the tumor cell lines are cultured. In a preferred embodiment, a plurality of tumor cell lines are used. Typically, at least ten tumor cell lines are used to obtain tumor cells. Cell lines for specific tumors are commercially available. For example, Example 1 provides 25 SCC cell lines. Examples of other SCC cell lines available from ATCC are: CRL-1550CCL-23, CRL-1554HTB-54, CRL-1555HTB-58, HTB-31CRL-1623, HTB-32CRL-1624, HTB-33CRL-1628, HTB-34CRL-1629, and HTB-35. Equal amounts of each tumor cell line are mixed together. Cell membranes are disrupted releasing cytoplasmic proteins and also releasing proteins loosely attached to the inner cytoplasmic membrane surface. These cytoplasmic proteins are separated from membrane and cytoplasmic organelles by ultracentrifugation. Because tumor cells are in various stages of cell division (mitosis) and/or because they are frequently lacking a nuclear membrane, the protein mixture would also comprise soluble nuclear proteins. A mixture of cytoplasmic proteins are covalently coupled to paper discs. The disc are incubated with cancer patient and control sera to measure IgA, IgE, IgM and/or IgG antibody levels.

Second, the intracellular protein mixture is fractionated into subfractions by ion-exchange chromatography (HPLC). A mixture of proteins in each fraction is covalently coupled to paper discs for antibody assays. Some of those fractions elicit higher antibody prevalence and/or titers among cancer patients. The subfractions eliciting higher serum antibody levels for tumor patients are further sub-fractionated to the individual molecule level by polyacrylamide gel electrophoresis (PAGE). Each positive protein fraction from the previous step is processed through PAGE followed by transfer to western blotting. Western blot positive (tumor patient positive only) bands are cut out for $NH_2$ terminus sequencing or intermediate peptide region amino acid sequencing.

Amino terminus sequence (or internal terminus sequence) of each protein is then used to construct nucleic acid probes and or immunogenic peptides for isolating DNA template sequence of the entire protein molecule. Template sequences are then used to construct expression systems for producing large amounts of specific proteins. The vector containing the template sequence is replicated by known methods in microorganisms, in insect cells or in mammalian cells.

Once isolated, tumor associated proteins are screened against control and tumor patient sera to identify those proteins that specifically immunoreact with sera from tumor patients. Means for determining immunoreactivity between antigens and sera (antibodies) are well known in the art. Means for determining immunoreactivity with specific immunoglobulins (e.g., IgA, IgE, IgG and IgM) are also well known in the art.

By way of example, IgA/IgG serum assays are used to detect antigens. These assays can be in the sandwich configuration with the antigen bound to a solid support. The solid support is contacted with serum containing antibodies. A labeled antibody immunoreactive with the bound antibody is added. Unbound reactants are removed. The amount of label can be correlated with IgA or IgG antibodies to antigen. This assay can also indicate which protein antigens or peptides are immunogenic for particular individuals (i.e. which proteins or peptides elicit specific T-helper cells in different individuals). In this embodiment at least one type of highly specific tumor antigen can be bound to a solid support and screened to determine immunoreactivity to IgA to IgG antibodies in serum.

In another embodiment, IgE serum assays are provided. In this assay, the antigen is bound to a solid support. The solid support is contacted with serum. The IgE antibodies bind to the antigen bound to the solid phase. A labeled antibody immunologically reactive to the IgE antibody is added to bind the IgE. Unbound reactant are removed. The presence or the amount of antigen reactive IgE correlates with the amount of labelled antibody. This test can also be used to indicate which tumor antigens or peptides are immunogenic for a particular individual (which proteins or peptides have already elicited specific T-helper cells in different individuals and thus which self proteins or peptides are recognizable by the patient's T cell immune system).

Before contacting sera with an antigen it is preferred (but not necessary) that the antigen be immobilized using conventional techniques. In one alternative embodiment, liposome-based assays may be used as described in more detail below. For conventional immobilization, polystyrene plates, for example, can be incubated with antigenic suspensions made in accordance with the invention. Alternatively, for example, antigens isolated as protein bands on electrophoretic gel can be transferred to a nitrocellulose sheet by known methods. See Towbin et al., *Proc. Nat'l. Acad. Sci.*, 76:4350–54 (1979); Burnette et al., *Biochem.*, 112:95–203 (1981). Numerous other techniques are known in the art for binding antigens to substantially inert substrates.

Bound antigens are contacted with a sample of sera to be tested for presence of antibody to antigen. The antigen and sera are preferably incubated for at least 5 to 15 minutes. Less time is needed when incubation proceeds at or near human body temperature, about 37° C. Incubation at other temperatures, for instance 4° C., is also proper, but generally requires additionally incubation time. The incubation time at 37° C. is from about 5 minutes to overnight. Rapid assays can also be performed at room temperature. The bound antigens should then be rinsed to remove any unbound antibodies, i.e., those which are not specific for the antigens. Preferably, rinsing proceeds with a buffer solution such as PBS T, PBS TT or Tris/Tween/Sodium chloride/azide. Multiple rinsing are preferred.

During incubation, tumor specific antibodies bind to the immobilized antigens to create antigen/antibody complexes. All unbound antibodies are substantially removed during the rinsing procedure. Due to the high specificity of the antigens of the invention, antibodies which are not specific for the tumor are substantially removed by the rinsing. Naturally, if the tested sample did not contain specific antibodies, the immobilized antigens would be substantially free of human antibody, and subsequent testing for antigen/antibody complexes should not indicate a substantial presence of such complexes. On the other hand, if the tested sample were rich in specific antibodies, these antibodies should have bound to the immobilized antigens to form a large quantity of antigen/antibody complex for subsequent detection.

Detection of antigen/antibody complex can be achieved by a wide variety of known methods. Preferred methods include but are not limited to enzyme-linked immunosorbent assay, latex agglutination, Western blot technique or indirect immunofluorescence assay.

Typically, the specific antibodies complexed with immobilized antigen are detected by contact with labeled or otherwise detectable second antibodies specific for the immunoglobulin being tested for. If the test sample is human sera, for example, the detectable second antibody is specific for human immunoglobulin. The second antibodies are preferably incubated with the immobilized antigens for about 5 minutes to overnight. An immunological excess of antibody is added, i.e. enough antibody or fragment thereof to bind the bound antigen. Then, the antigens are washed with a buffer solution (preferably multiple times) in order to remove all unbound labeled antibody. The washing will remove substantially all labeled antibody except that which has bound to immunoglobulin present on the antigens. Of course, substantially the only human immunoglobulin present at this point should be tumor specific antibody. Hence, the presence of tumor specific antibody can be indirectly measured by determining the presence or absence of the labeled second antibody.

There are many known techniques for detecting the label, which vary with the type of label used. For instance, fluorescein-labeled antibody can be detected by scanning for emitted light at the characteristic wavelength for fluorescein. Alternatively, an enzyme label is detected by incubation with appropriate substrates and detection of an enzyme activity, preferably activity resulting in a color change. Such activity can be determined by visual inspection or can be read automatically by a spectrophotometer set at the appropriate wavelength.

Alternatively, the enzyme label can be horseradish peroxidase and the substrate can be $H_2O_2$ and 2,2'-azinobis(3-ethylbenzothiazoline-6-sulfonic acid) which produces in the presence of the enzyme, a compound detectable by a spectrophotometer set at 414 nm.

In Western blotting, the positive signal can be detected when an enzyme is conjugated to the second antibody. Incubation with appropriate substrate enzymatically produces a color product in the immediate vicinity of the antigenic band resolved by this process. The presence of a reactive band can be detected by visual inspection. In an indirect immunofluorescence assay, fluorescein-labeled second antibodies can be detected by fluorescence-activated detectors, or by visual inspection.

A liposome-based assay can involve the presence of fluorescein, an enzyme or a substrate inside a liposome onto whose surface tumor antigens are expressed. These liposomes are incubated with a diluted body fluid sample to be tested, and are thoroughly washed. Any liposome with immunoglobulins on their surface forming an antigen/ antibody complex can be recognized by attaching a second antibody, specific to the immunoglobulin being tested for, on to the inside walls of a polystyrene tube containing the liposomes. Liposomes having antibody bound to their surfaces will become immobilized on the tube walls, and non-immobilized liposomes will be washed away. The liposomes can by lysed with, for instance, detergent, or complement, and the enzyme or substrate that was in the interior is now free to react with the complementary substrate (or enzyme) in the solution in the tube. Enzymatic activity, preferably a color change reaction could be detected by visual inspection or spectrophotometric color determination. Enzymatic activity beyond the predetermined positive threshold indicates the presence of tumor specific antibodies.

Any sample suspected of containing antibodies may be tested in accordance with the methods set forth herein. Preferably, the samples to be tested are bodily fluids such as blood, serum, urine, tears, saliva and the like. In addition to human samples, samples may be taken from mammals such as non-human primates, horses, swine, etc. Due to the sensitivity of the test described, it is possible to dilute the sample prior to testing. Dilution can proceed by addition of any fluid compatible with each of the sample, the antibodies to be tested, and the antigenic composition. Serum, when used as the sample, can, for example, be diluted with one or more fluids selected from the group consisting of phosphate-buffered saline, pH 7.0–7.4 (hereinafter, "PBS"), PBS-containing TWEEN 20™ (hereinafter, "PBS T"); PBS T with thimerosal (hereinafter, "PBS" TT), PBS TT with gelatin (hereinafter, "PBS TTG"), and PBS TTG with bovine gamma globulin (hereinafter, "PBS TTGG"). Dilutions, when testing for IgG antibody, may be as high as a ratio from about 1:100 to about 1:1000.

Once tumor specific antigens have been identified through screening, those antigens are isolated and purified using standard techniques well known in the art. The identification and preparation of tumor specific antigens from SCC and breast cancer are described in detail hereinafter in the Examples.

The present invention also contemplates a tumor specific antigen preparable by such a process. In one preferred embodiment, a tumor specific antigen is a SCC antigen such as SCC antigen 3.3, 16.1, 16.3, 16.4, 27.3, 35.1, 37.1, 37.2, 39.1, 39.2, 39.4, 40.1, 40.3, 40.4, 47.2, 47.3, 47.4, 49.2, 49.3, 50.1, 50.2 or 50.3.

In another preferred embodiment, a tumor specific antigen is a breast cancer specific antigen such as phosphorylated dbl. In one embodiment, dbl is p66 dbl, which dbl preferably comprises the amino acid residue sequence of SEQ ID NO:2. Phosphorylated dbl comprises, in various embodiments, one or more phosphorylated serine, threonine or tyrosine residues.

Where phosphorylated dbl comprises at least one phosphorylated serine residue, that residue is preferably located at amino acid residue position number 2, 3, 9, 23, 25, 47, 151, 202, 295, 299, 402, 436, 438, or 442 of SEQ ID NO:2. Where phosphorylated dbl comprises at least two phosphorylated serine residues, those residues are preferably located at amino acid residue position numbers 2 and 3, 2 and 9, 3 and 9, 23 and 25, 295 and 299, 436 and 438, 436 and 442, or 438 and 442 of SEQ ID NO:2. Where phosphorylated dbl comprises at least three phosphorylated serine residues, those residues are preferably located at amino acid residue position numbers 2, 3 and 9 or 436, 438 and 442 of SEQ ID NO:2.

Where phosphorylated dbl comprises at least one phosphorylated threonine residue, that residue is preferably located at amino acid residue position number 38, 263, 380, 403 or 406 of SEQ ID NO:2. Where phosphorylated dbl comprises at least two phosphorylated threonine residues, those residues are preferably located at amino acid residue position numbers 403 and 406 of SEQ ID NO:2.

Where phosphorylated dbl comprises at least one phosphorylated tyrosine residue, that residue is preferably located at amino acid residue position number 201 of SEQ ID NO:2.

Phosphorylated dbl can also comprise more than one type of phosphorylated amino acid residue. In one embodiment, phosphorylated dbl comprises at least on e phosphorylated serine residue and at least one phosphorylated threonine residue, preferably wherein a) two phosphorylated serine residues are located at amino acid residue position numbers 23 and 25 of SEQ ID NO:2 and one phosphorylated threonine residue is located at amino acid residue position number 38; b) one phosphorylated serine residue is located at amino acid residue position number 402 of SEQ ID NO:2 and two phosphorylated threonine residues are located at amino acid residue position numbers 403 and 406 of SEQ ID NO:2; or c) one phosphorylated serine residue is located at amino acid residue position number 402 of SEQ ID NO:2 and one phosphorylated threonine residue is located at amino acid residue position number 403 or 406 of SEQ ID NO:2.

Where phosphorylated dbl comprises at least one phosphorylated serine residue and at least one phosphorylated tyrosine residue, those residues are preferably situated wherein one phosphorylated serine residue is located at amino acid residue position number 202 of SEQ ID NO:2 and one phosphorylated tyrosine residue is located at amino acid residue position number 201 of SEQ ID NO:2. In another embodiment, phosphorylated dbl comprises the amino acid residue sequence of SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38.

B. Tumor Cell Functional Protein

In another aspect, the present invention provides a process of identifying a functional protein of a tumor cell comprising identifying a protein present in the tumor cell that is selectively immunogenic for tumor patients. In one embodiment, the tumor cell is a SCC cell or a breast cancer cell. In another preferred embodiment, the functional protein is selectively functional for the tumor cell.

As used herein, a functional protein of a tumor cell means a protein expressed in a tumor cell and which protein functions in maintaining tumor cell viability. A tumor cell functional protein can also be expressed in normal, non-tumor cells. A tumor cell functional protein can be selectively functional in a tumor cell. In this latter case, either that protein is not expressed in a normal cell, is expressed in a form different from the form in the tumor cell or is expressed at such a low level in the normal cell that it does not participate in normal cell function to a measurable degree.

In another aspect, the present invention provides a process of making a functional protein of a tumor cell comprising the steps of (a) identifying a protein present in the tumor cell, which protein is selectively immunogenic for tumor patients; and (b) isolating and purifying the protein. The present invention also contemplates a protein made by that process. In another embodiment, a process of making a functional protein of a tumor cell further comprises the steps of (c) sequencing the isolated and purified protein; (d) preparing a polynucleotide that encodes the sequenced protein; (e) transfecting a host cell with an expression vector comprising the polynucleotide; (f) maintaining the transfected host cell under conditions sufficient for expression of the protein; and (g) collecting the protein.

It will be readily apparent to a skilled artisan that tumor specific antigens can be tumor cell selectively functional proteins. The present invention also discloses selectively functional tumor cell proteins. As set forth hereinafter in Example 1, SCC antigen 3.3 is likely a such a functional protein. The amino terminus of SCC 3.3 has been sequenced and found to have the partial amino acid residue sequence Gln-Phe-Pro-Phe-Gly-Ala-Gly-Glu-Thr (SEQ ID NO:1). That sequence matches with the E6 protein of human papillomavirus, which protein is an oncogene that functions to promote tumor growth and development.

As disclosed above, the present invention has identified phosphorylated dbl as a breast cancer specific antigen. Dbl is likely a breast cancer selectively functional protein. The dbl oncogene product is a 66 kD cytoplasmic phosphoprotein distributed between the cytosolic and the cytoskeletal matrix-associated cell membrane fractions (Srivastava et al., Identification of the protein encoded by the human diffuse B-cell lymphoma(dbl) oncogene. Proc Natl Acad Sci U S A 1986;83(23):8868–72) that was isolated by Eva and Aaronson through the transfection of NIH/3T3 cells employing the DNA of human B-cell lymphoma (Eva et al., Isolation of a new human oncogene from a diffuse B-cell lymphoma. Nature 1985;316(6025):273–5). Its normal homologue is the 115 kD dbl proto-oncogene product (p115 dbl) composed of 925 amino acids (Ron et al., Molecular cloning and characterization of the human dbl proto-oncogene: evidence that its overexpression is sufficient to transform NIH/3T3 cells. Embo J 1988;7(8):2465–73). p66 dbl is composed of 478 amino acids (Eva et al., The predicted DBL oncogene product defines a distinct class of transforming proteins. Proc Natl Acad Sci U S A 1988;85(7):2061–5). It is a fusion protein whose terminal 428 amino acid residues correspond to the terminal residues of the p 115 molecule. p66 dbl possesses an additional 50 amino acid portion not present on the dbl proto-oncogene product (Eva et al., The predicted DBL oncogene product defines a distinct class of transforming proteins. Proc Natl Acad Sci U S A 1988;85(7):2061–5), which residues, however, are incorporated from a yet unknown gene source. Both p66 and p115 dbl are phosphorylated at serine residues with some occasional threonine phosphorylation (Graziani et al., The human dbl-proto-oncogene product is a cytoplasmic phosphoprotein which is associated with the cytoskeletal matrix. Oncogene 1989;4(7):823–9). p66 dbl possesses a phosphorylated intracellular half-life of 6 hours compared to the 1 hour for the proto-oncogene product (Graziani et al., The human dbl-proto-oncogene product is a cytoplasmic phosphoprotein which is associated with the cytoskeletal matrix. Oncogene 1989;4(7):823–9). p66 dbl has also been shown to contain more phosphorylated residues than p115 dbl. Like the corresponding p115 proto-oncogene product, p66 dbl likely functions as a GDP-GTP exchange factor for a ras-like polypeptide such as cdc24 found in yeast cells (Adams et al., The hematopoietically expressed vav proto-oncogene shares homology with the dbl GDPro-GTP exchange factor, the bcr gene and a yeast gene (CDC24) involved in cytoskeletal organization. Oncogene 1992;7(4):611–8).

C. Kits and processes for detecting antibodies to tumor specific antigens

In another aspect, the present invention provides an assay kit for detecting the presence of an antibody immunoreactive with a tumor specific antigen comprising, in an amount sufficient for at least one assay, a tumor-specific antigen. A tumor specific antigen used in a kit is the same as set forth above. The tumor specific antigen is preferably SCC antigen 3.3, 16.1, 16.3, 16.4, 27.3, 35.1, 37.1, 37.2, 39.1, 39.2, 39.4, 40.1, 40.3, 40.4, 47.2, 47.3, 47.4, 49.2, 49.3, 50.1, 50.2 or 50.3 or phosphorylated dbl. The kit can further comprise means for detecting the antibody immunoreacted with the tumor-specific antigen (e.g., an antigen-antibody conjugate or complex). The antibody is an IgA, IgE, IgG or IgM immunoglobulin. Means for detecting antigen-antibody complexes are set forth above.

In still yet another aspect, the present invention provides a process of detecting the presence in a biological fluid of an antibody immunoreactive with a tumor-specific antigen, the process comprising the steps of: (a) forming an admixture with a sample of the body fluid and the tumor-specific antigen; (b) maintaining the admixture under biological reaction conditions for a period of time sufficient for formation of a conjugate between antibody present in the sample and the tumor-specific antigen; and (c) detecting the presence of the conjugate. The tumor specific antigen is preferably SCC antigen 3.3, 16.1, 16.3, 16.4, 27.3, 35.1, 37.1, 37.2, 39.1, 39.2, 39.4, 40.1, 40.3, 40.4, 47.2, 47.3, 47.4, 49.2, 49.3, 50.1, 50.2, 50.3 or phosphorylated dbl. The antibody is an IgA, IgE, IgG or IgM immunoglobulin.

Preferred techniques for detecting formation of antigen-antibody conjugates, as set forth above, include, but are not limited to, enzyme-linked immunosorbent assay (ELISA), indirect immunofluorescence assay, latex agglutination, and liposome-based assay. Alternatively, a Western blot technique may be used, in which case the bands are detected by visual inspection, and substantial appearance of dark bands may be taken as a positive indication. The extent of detection of the antigen/antibody complex which should be considered a positive signal (i.e., an indication that the test sample includes SCC-specific antibody) depends upon the detection means chosen, but may be defined generically as a value greater than the mean plus 1 interval of standard deviation from the results observed with samples from a negative control group, all other parameters (dilution of sample, time of incubation, etc.) being held constant. In some embodiments where higher specificity is desired, the mean plus two or mean plus three standard deviations may be utilized. The negative control group should consist of individuals who are known to be free of tumor specific antigens.

D. A process of making/preparing a population of T cells sensitized to a tumor specific antigen The present invention provides the identification of tumor antigens that can be used to generate anti-tumor effector cells. Tumor antigens can be capable of inducing the development of T cells that are effective in recognizing and destroying tumor cells. By way of background, cells such as B and T lymphocytes act as effectors of the immune system. These lymphocytes are respectively involved in mounting a humoral and cell-mediated response to foreign antigens. Mature B and T cells bear receptors specific for distinct antigens. Mature T lymphocytes express the CD3 cell surface molecule. Two principal categories of T cells can play major roles in tumor therapy, CD8+ T cells cytotoxic T-cells (CTL) and CD4+ T cells (T helper cells). In general, CD8+ cells are considered to mediate direct killing and CD4+ cells are considered to mediate an antitumor effect by secretion of cytokines such as Interleukin 2, tumor necrosis factor, lymphotoxin, interferon, colony stimulating factors and macrophage activating factors that have direct and/or indirect anti-tumor activity. However, CD8+ T cells and CD4+ T cells can have overlapping function (i.e. CD4+ cells can kill by direct lysis and CD8+ cells can function by secreting cytokines). The major distinction between CD8+ and CD4+ T cells is that CD8+ T cells recognize antigen presented by class I MHC molecules and CD4+ T cells recognize antigen presented by class II MHC molecules. In general, the internal antigens synthesized by the target cell enter the class I MHC antigen presenting pathway to the exclusion of antigens in the external cell environment. Antigens in the external cell environment, including secreted self proteins and internal proteins released by tumor cell death and breakdown enter the class II MHC antigen process pathway and stimulate CD4+ cells. In most normal immune responses, both CD8+ and CD4+ T cells participate. However, either subset alone is capable of mediating tumor therapy.

The present invention thus provides a process of preparing a population of T cells sensitized to a tumor-specific antigen comprising the steps of: (a) isolating T cells sensitized to the tumor-specific antigen; and (b) inducing numerical expansion of the sensitized T cells. Inducing is preferably accomplished in the presence of the tumor-specific antigen and, if necessary, antigen presenting cells. The T cells used in this process are preferably isolated from circulating lymphocytes, lymph nodes or tumors. This process can further comprise the step of: (c) sub-culturing the T cells to identify T cells sensitized to a particular tumor-specific epitope.

Techniques have been developed to expand immune T cells to large numbers by specific activation in vitro with antigen, followed by repetitive cycles of restimulation with antigen, mononuclear feeder cells and IL-2. See Cheever et al., *J. Immunol.* 126:1318 (1981); Cheever et al., *J. Exp. Med.* 155:968 (1982) and Cheever et al. *J. Exp. Med.* 163:1100 (1986). It should be noted that in humans truly syngeneic tumor cells are available only from identical twins. Autologous tumor cells are infrequently available for a variety or reasons, including insufficient tumor sample and difficulty in tumor cell culture and expansion. While feeder cell provisions can theoretically be achieved with irradiated autologous, leukophoresed cells, the issue of antigen availability remains unsolved. The present invention provides a solution to this problem in that a library of antigens sufficient to provoke an immunogenic repertoire descriptive of all derivative cells of each tumor type is contemplated. A description of a peptide library of tumor specific antigens is set forth hereinafter.

More specifically, SCC antigens are recognized by specific T-helper lymphocytes as these immune cells are required for the production of IgA, IgE and IgG by B-lymphocytes. This invention provides antigens which are recognized by tumor-reactive T-helper (Th) and cytotoxic T lymphocytes (CTL). These lymphocytes can be cloned and expanded to provide autologous Th cells and/or CTL using antigenic peptides shown to bind to individual patient MHC I or II molecules. The cloned lymphocytes can be frozen to provide multiple treatment sets. The treatment would involve the infusion of large amounts of tumor-targeted Th cells and/or CTL to effect tumor cell killing and eradication. A further benefit of this treatment regimen is that T-helper memory cells remain after tumor eradication to prevent tumor recurrence. The cells can be expanded to approximately $10^8$ to $10^{10}$ cells in culture. Adoptive transfer of up to $5 \times 10^{10}$ cells has not been associated with significant toxicity. The immunogenic tumor specific antigen is preferably SCC antigen 3.3, 16.1, 16.3, 16.4, 27.3, 35.1, 37.1, 37.2, 39.1, 39.2, 39.4, 40.1, 40.3, 40.4, 47.2, 47.3, 47.4, 49.2, 49.3, 50.1, 50.2, 50.3 or phosphorylated dbl.

In an alternative embodiment where the patient does not produce immune T cells in recoverable quantities, lymphocytes can be activated in vitro. In another aspect, therefore, the present invention provides a process of making T cells sensitized to a tumor-specific antigen. That process comprises the steps of: (a) isolating a population of autologous T cells containing virgin non-antigen sensitized T cells; (b) identifying an immunogenic tumor-specific antigen; and (c) sensitizing the non-antigen sensitized T cells with the immunogenic tumor-specific antigen. The tumor specific antigen is preferably SCC antigen 3.3, 16.1, 16.3, 16.4, 27.3, 35.1, 37.1, 37.2, 39.1, 39.2, 39.4, 40.1, 40.3, 40.4, 47.2, 47.3, 47.4, 49.2, 49.3, 50.1, 50.2, 50.3 or phosphorylated dbl. The T cells are preferably T-helper lymphocytes or specific cytotoxic T cells.

T cells which are specific for antigens expressed by tumor can be used to treat malignant tumors. As an example, T-cells specific for a particular type of tumor antigen can be isolated and administered to a patient having a tumor. Tumor specific T cells can be generated in vitro and used to treat cancer patients. See Rosenberg et al., N. Engl. J. Med. 319:1767 (1988). This type of therapy has been referred to as adoptive immunotherapy. T cells specific for certain tumor antigens can be isolated from a subject, expanded and readministered to a patient in sufficient quantity to eliminate the tumor cells. See Riddle et al., *J. Immunol. Meth.* 128: 189 (1990). See Example 1, J. iv & v for additional detail.

In another embodiment tumor antigens can be used to develop a cancer vaccine for carcinoma. In this embodiment, Vaccinia or another carrier virus containing nucleic acids that encode tumor antigens matching the individual patient MHC framework are constructed. See Mackett, *Proc. Nat'l Acad. Sci. USA* 79:7415–19 (1982); Mackett, *J. Virol.* 49: 857–65 (1984). This vaccine can be administered in a pharmaceutically acceptable carrier.

E. Increasing the immunospecificity of tumor associated proteins

In yet another aspect, the present invention provides a process of increasing the immunogenic specificity of a tumor-associated antigen comprising phosphorylating the tumor-associated antigen. Preferably the tumor antigen is a breast cancer antigen such as dbl that comprises the amino acid residue sequence of SEQ ID NO:2.

As set forth above, phosphorylated dbl is a breast cancer specific antigen. Phosphorylated p66 dbl specifically immunoreacts with sera from tumor patients as compared to sera from normal, non-breast cancer patients. Example 2 sets forth details concerning the increased immunospecificity of phosphorylated dbl.

The phosphorylation of dbl that leads to its increased immunospecificity for tumor sera can result from an increased or aberrant phosphorylation of serine, threonine or tyrosine residues.

Where phosphorylated dbl comprises at least one phosphorylated serine residue, that residue is preferably located at amino acid residue position number 2, 3, 9, 23, 25, 47, 151, 202, 295, 299, 402, 436, 438, or 442 of SEQ ID NO:2. Where phosphorylated dbl comprises at least two phosphorylated serine residues, those residues are preferably located at amino acid residue position numbers 2 and 3, 2 and 9, 3 and 9, 23 and 25, 295 and 299, 436 and 438, 436 and 442, or 438 and 442 of SEQ ID NO:2. Where phosphorylated dbl comprises at least three phosphorylated serine residues, those residues are preferably located at amino acid residue position numbers 2, 3 and 9 or 436, 438 and 442 of SEQ ID NO:2.

Where phosphorylated dbl comprises at least one phosphorylated threonine residue, that residue is preferably located at amino acid residue position number 38, 263, 380, 403 or 406 of SEQ ID NO:2. Where phosphorylated dbl comprises at least two phosphorylated threonine residues, those residues are preferably located at amino acid residue position numbers 403 and 406 of SEQ ID NO:2.

Where phosphorylated dbl comprises at least one phosphorylated tyrosine residue, that residue is preferably located at amino acid residue position number 201 of SEQ ID NO:2.

Phosphorylated dbl can also comprise more than one type of phosphorylated amino acid residue. In one embodiment, phosphorylated dbl comprises at least one phosphorylated serine residue and at least one phosphorylated threonine residue, preferably wherein a) two phosphorylated serine residues are located at amino acid residue position numbers 23 and 25 of SEQ ID NO:2 and one phosphorylated threonine residue is located at amino acid residue position number 38; b) one phosphorylated serine residue is located at amino acid residue position number 402 of SEQ ID NO:2 and two phosphorylated threonine residues are located at amino acid residue position numbers 403 and 406 of SEQ ID NO:2; or c) one phosphorylated serine residue is located at amino acid residue position number 402 of SEQ ID NO:2 and one phosphorylated threonine residue is located at amino acid residue position number 403 or 406 of SEQ ID NO:2.

Where phosphorylated dbl comprises at least one phosphorylated serine residue and at least one phosphorylated tyrosine residue, those residues are preferably situated wherein one phosphorylated serine residue is located at amino acid residue position number 202 of SEQ ID NO:2 and one phosphorylated tyrosine residue is located at amino acid residue position number 201 of SEQ ID NO:2. In another embodiment, phosphorylated dbl comprises the amino acid residue sequence of SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38.

F. Peptide Library of tumor specific antigens

The present invention provides a process of making a peptide library of tumor specific humoral antigens. That process comprises the steps of: (a) isolating one or more selectively immunogenic proteins from tumor cells; (b) identifying in each of the selectively immunogenic proteins one or more epitopes that are selectively immunogenic for tumor patients; (c) preparing for each epitope a peptide that contains the epitope, wherein no single peptide contains an epitope recognized by non-tumor subjects; and (d) forming a library of the peptides.

In one embodiment, isolating comprises the steps of: (a) extracting proteins from a tumor cell; (b) screening control and tumor patient sera to determine which of the proteins specifically immunoreact with an antibody in tumor patient sera; and (c) isolating and purifying the selectively immunogenic protein. Means for isolating proteins from tumor cells and screening those proteins with control and tumor patient sera to determine those proteins that specifically immunoreact with tumor patient sera have been set forth above.

Identifying preferably comprises the steps of: (a) defining potential epitopes in the protein; (b) synthesizing peptides comprising a portion of the protein, which portion contains one of the epitopes; and (c) screening control and tumor patient sera to determine which of the proteins specifically immunoreact with an antibody in tumor patient sera and thus identifying epitopes in the protein that are selectively immunogenic for tumor patients.

Various means well known in the art can be used to identify potential epitopes in tumor specific antigens. By way of example, antigens can be sequenced to determine their amino acid residue sequence and that sequence compared to previously identified epitopes. Where the epitope involves a phosphorylated residue, a rolling sum analysis can be used to identify potential phosphorylation sites. The disclosure of the use of such a rolling sum analysis as it applies to phosphorylate dbl is set forth hereinafter.

Once potential epitopes are defined, peptides containing at least one such epitope are made. Although a single peptide can comprise more than one potential epitope, no single peptide contains an epitope that immunoreacts with serum from a non-tumor subject. Means for synthesizing proteins are well known in the art.

Peptides are constructed to a length of 20 amino acids comprising those amino acid residue sequences defined in this section plus additional non-specific spacer amino acid residues (glycine or alanine) added to each individual peptide so as to project it from its point of conjugation to human serum albumin (HSA) (Emini et al., Priming for and induction of anti-poliovirus neutralizing antibodies by synthetic peptides. *Nature* 1983;304(5928):699–703; McMillan et al., Synthetic idiotypes: the third hypervariable region of murine anti-dextran antibodies. *Cell* 1983;35(3 Pt 2):859–63; Makela et al., In: Weir DM, ed. Handbook of experimental immunology. *Oxford: Blackwell Scientific Publications,* 1986:1). In addition, each peptide has at its amino- or carboxy- terminal a non-specific cysteine residue to couple it covalently to its carrier HSA via an N-succinimidyl 3-(2-pyridyldithio)propionate (SPDP) linkage (Carlsson et al., Protein thiolation and reversible protein—protein conjugation. N-Succinimidyl 3-(2-pyridyldithio)propionate, a new heterobifunctional reagent. *Biochem J* 1978;173(3) :723–37; Lee et al., A method for preparing beta-hCG COOH peptide-carrier conjugates of predictable composition. *Mol Immunol* 1980; 17(6):749–56). Where the peptide already possesses cysteine residues, no specific linker amino acids are added. Instead, the carbodiimide method is used to link each peptide to HSA (Van Regenmortel et al., Synthetic polypeptides as antigens. Amsterdam, New York & London: Elsevier, 1988(Burden R H. van Knippenberg P H, ed. Laboratory Techniques in *Biochemistry and Molecular Biology*).

Each peptide is preferably covalently coupled to HSA. A carrier molecule is required to predictably provide a sufficient quantity of peptide for analysis and also to give each peptide a more natural projection for facilitated antibody coupling. Individual peptides are coupled to HSA molecules at high molar ratios (>10:1, peptide:HSA) employing predictable conjugation methods (61–66). HSA is used as an exemplary preferred carrier molecule because it should react minimally with autologous antibody as compared to using non-self carrier proteins such as bovine serum albumin (BSA). Peptides are preferably coupled to the free amino groups on the surface of HSA molecules.

Tumor patient and control sera are tested against a mixture of HSA-peptide conjugates. The HSA-peptide mixture is analyzed using our standard western blot method. A mixture of all possible peptide permutations is employed to identify those sera, tumor and control, reacting with any individual peptide. To minimize non-cancer-specific epitope reactions, each tested serum sample can be spiked with a non-epitope equivalent of peptides. Those peptides are conjugated to HSA and used in a mixture to inhibit serum antibodies recognizing the non-specific epitopes of each peptide. Those antibodies (likely in cancer patient sera only) that react with the tumor-specific epitopes are likely left uninhibited. The antibody isotypes tested are IgA, IgG, IgM, and IgE. Individual patients likely produce different reactive antibody isotypes in response to any given immunogenic protein.

The prevalence of IgM production among patients with early stage disease as compared to later stages would strongly suggest that even earlier detection, at the carcinoma in situ (CIS) stage, might be possible by measuring IgM reactivity. IgE reactivity is analyzed to test the premise that IgG-producing sensitization requires prolonged antigen exposure and therefore not likely to be a useful isotype in early tumor detection. Any such reactivity is therefore analyzed in the context of the corresponding stage of tumor development of the tested serum.

Serum samples from patients with all stages of tumor development are tested along with control samples obtained from patients with benign lesions and healthy subjects.

All initially reactive patient and control sera are retested against individual HSA-peptide conjugates. Sera reacting in a positive fashion with the mixture of HSA-peptide conjugates is used to test the humoral reactivity of each individual conjugate. The assay methodology remains the same. However, the spiking antigen is, in each case, the corresponding non-epitope HSA conjugate and not the spiking conjugate mixture. Those peptides which react only with tumor patient sera are analyzed further.

The longest possible, tumor-specific, amino acid sequence on either side of each epitope are mapped out. A successful conclusion of this task provides peptides which function as a tumor-specific immunogens and also serves as ideal source antigen for constructing tumor-specific serum antibody assays without the need of preparative antigen spiking. Delineation of the largest possible tumor-specific immunogenic domain would provide enough binding site for most available serum antibodies to react with even though these may vary ever so slightly in their structural recognition of the epitope region. This would increase assay sensitivity. In proceeding thus, we may find epitope specificity well beyond the 5–6 amino acid reach of a particular epitope. This might occur because of a change in distal peptide conformation brought on by salt bridging between the epitope and distal amino acids (Otovos et al., Phosphorylation loops in synthetic peptides of the human neurofilament protein middle-sized subunit. *J Protein Chem* 1988;7 (4):365–76). Various shorter versions of the peptides identified as being tumor-specific are synthesized and tested against the positive tumor sera and control sera. The control sera tested consists of a statistically significant number of samples obtained from patients with benign lesions and from healthy controls.

The present invention also contemplates a library prepared by this process.

In a preferred embodiment, the epitope comprises an aberrantly phosphorylated amino acid residue sequence. Proteins able to undergo intracellular phosphorylation are the target group at-large. A list representative of this group is provided in FIG. 11. Its members include oncogene-encoded proteins, phosphorylated receptor proteins, cellular kinases, cell cycle proteins, transcription factors and others. Candidate molecules likely include: (1) proteins which are qualitatively and/or quantitatively specific for cancer cells versus normal cells; (2) proteins which are phosphorylated for very short durations in normal cells but remain phosphorylated longer in cancer cells; (3) proteins which are closely associated with cellular proliferation; and (4) proteins which occur in embryological tissues, are absent in normal post-fetal tissues, but are expressed in breast cancer cells.

Candidate proteins are selected based on a review of the scientific literature. Citations dealing with oncogene-transcribed proteins, phosphorylated receptors, cellular kinases, cell cycle proteins, transcription factors and other phosphorylated proteins are analyzed for descriptions of qualitative and/or qualitative specificity. Relative specificity is delineated on the basis of immunohistochemical analysis, RNA and/or DNA hybridization, and specific protein isolation work.

Candidate proteins are also selected on the basis of our ongoing immunohistochemical analysis of breast cancer tissues. Initial candidates are oncogene-encoded proteins testing positive in other tumor systems, other oncogene-encoded proteins, phosphorylated receptors, cellular kinases, cell cycle proteins, transcription factors and other proteins associated with cellular proliferation and/or differentiation.

Candidate proteins can also be selected on the basis of information derived from attempts to isolate cytoplasmic proteins from breast cancer cells which serve as selectively specific humoral immunogens. Established cell lines such as BThr-20, BThr-474, BThr-483, MCF-7, MDAla-MB-134, MDAla-MB-157, MDAla-MB-231, MDAla-MB-453, MDAla-MB-468 and SKBArg-3 (American Tissue Type Collection, Rockville, Md.), are cultured to a 50 mL packed-cell volume. Soluble proteins are extracted from each cell pellet in aqueous buffer and sub-fractionated using several different chromatographic steps. The soluble proteins are fractionated by DEAE anion-exchange chromatography, followed by SP cation-exchange chromatography. Individual, protein-containing fractions derived from the DEAE and SP chromatography are run on 7.5 and 15.0 percent polyacrylamide gels (PAGE) and transferred to nitrocellulose paper for western blot analysis of individual breast cancer cell proteins. Once thus identified, such proteins are electrophoretically transferred onto polyvinylidene fluoride (PVDF) membranes and sent for partial amino acid sequencing. Derivative amino acid sequences permit the identification of proteins whose full amino acid sequences are already known. If the derivative amino acid sequences are to proteins not previously described, they are employed as nucleic acid templates to be used in delineating the genomic sequences of those molecules.

As set forth above, phosphorylated dbl has been identified as a breast cancer-specific antigen. In another aspect, therefore, the present invention provides a process of making a peptide library of breast cancer specific humoral antigens comprising the steps of: (a) identifying proteins present in breast cancer cells that are selectively immunogenic for breast cancer patients; (b) defining potential phosphorylation sites of the proteins; (c) synthesizing peptides comprising a portion of the protein, which portion contains at least one of the phosphorylation sites and wherein at least one of the phosphorylation sites is phosphorylated; (d) screening the peptides to identify phosphorylated peptides that are selectively immunogenic for breast cancer patients; and (e) forming a library of the phosphorylated selectively immunogenic peptides. In one embodiment, the protein is an oncogene-transcribed protein, a cell-cycle protein, a receptor, a transcription factor or other regulatory protein or substrate protein.

In another embodiment of that process, the protein is dbl and the potential phosphorylation sites comprise: (a) a phosphorylated serine residue at amino acid residue position number 2, 3, 9, 23, 25, 47, 151, 202, 295, 299, 402, 436, 438, or 442 of SEQ ID NO:2; (b) at least two phosphorylated serine residues located at amino acid residue position numbers 2 and 3, 2 and 9, 3 and 9, 23 and 25, 295 and 299, 436 and 438, 436 and 442, or 438 and 442 of SEQ ID NO:2; (c) at least three phosphorylated serine residues located at amino acid residue position numbers 2, 3 and 9 or 436, 438 and 442 of SEQ ID NO:2; (d) a phosphorylated threonine residue located at amino acid residue position number 38, 263, 380, 403 or 406 of SEQ ID NO:2; (e) at least two phosphorylated threonine residues located at amino acid residue position numbers 403 and 406 of SEQ ID NO:2; (f) at least one phosphorylated tyrosine residue located at amino acid residue position number 201 of SEQ ID NO:2; (g) at least one phosphorylated serine residue and at least one phosphorylated threonine residue wherein (i) the phosphorylated serine residue is located at amino acid residue position numbers 23 and 25 of SEQ ID NO:2 and one phosphorylated threonine residue is located at amino acid residue position number 38;

(ii) one phosphorylated serine residue is located at amino acid residue position number 402 of SEQ ID NO:2 and two phosphorylated threonine residues are located at amino acid residue position numbers 403 and 406 of SEQ ID NO:2; or iii) one phosphorylated serine residue is located at amino acid residue position number 402 of SEQ ID NO:2 and one phosphorylated threonine residue is located at amino acid residue position number 403 or 406 of SEQ ID NO:2; or (h) at least one phosphorylated serine residue and at least one phosphorylated tyrosine residue wherein the phosphorylated serine residue is located at amino acid residue position number 202 of SEQ ID NO:2 and the phosphorylated tyrosine residue is located at amino acid residue position number 201 of SEQ ID NO:2. The protein portion in the above process preferably comprises the amino acid residue sequence of SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38.

Screening of a large number of synthesized candidate peptides for breast cancer-specific serum antibody reactivity yields a library of tumor-specific peptides. This library is then used as a source of antigens with which to construct a highly sensitive and specific serologic assay for detecting early breast cancer in most patients.

The complete amino acid sequence of p66 dbl has been described by Eva (Eva et al., The predicted DBL oncogene product defines a distinct class of transforming proteins. *Proc Natl Acad Sci U S A* 1988;85(7):2061–5). Using a compendium of four individual procedures used to delineate surface peptides, we have mapped out those amino acid residues most likely to qualify as candidate sites for phosphorylation. Employing a rolling sum analysis of 7 consecutive residues, the individual methods used to construct the unified analysis included a determination of hydrophilicity (Hopp et al., Prediction of protein antigenic determinants from amino acid sequences. *Proc Natl Acad Sci USA* 1981;78(6):3824–3828), HPLC peptide retention index (Parker et al., New hydrophilicity scale derived from high-performance liquid chromatography peptide retention data: correlation of predicted surface residues with antigenicity and x-ray-derived accessibility sites. *Biochemistry* 1986;25:5425–5432), hydrophobicity index (Fauchere J L, Pliska V. Hydrophobic parameters pi of amino-acid side chains from the partitioning of Asn-acetyl-amino-acid amides. *Eur J Med Chem* 1983; 18(4):369–375), and accessibility index (Fraga et al., Prediction of the secondary structure and functional sites of major histocompatibility complex molecules. *J Mol Recognit* 1990;3(2):65–7347).

Potential phosphorylation sites include serine, threonine and tyrosine residues. Aberrant phosphorylation of dbl associated with breast cancer can occur at a plurality of sites and involve more than one type of residue. The combined rolling sum analysis of p66 dbl is illustrated in FIG. 10. The peptide regions qualifying for external exposure are illustrated in FIG. 10. Based on the above analysis, the p66 dbl peptide sequences having greatest potential for serine phosphorylation include those sequences designated SEQ ID NOs: 3–10, where the phosphorylated residues are underlined:

Met-<u>Ser</u>-<u>Ser</u>-Gly-Arg-Arg-Gly-<u>Ser</u> (SEQ ID NO:3)
<u>Ser</u>-Pro-<u>Ser</u>-Arg-Asp-Lys-Glu-Glu-Glu-Glu-Glu-Arg-Pro-Gly-Thr(SEQ ID NO:4)
Ala-Pro-Gly-Arg-<u>Ser</u>-Ala-Ala (SEQ ID NO:5)
Cys-Gln-Asn-Lys-Pro-Arg-<u>Ser</u> (SEQ ID NO:6)
Glu-Leu-Leu-Lys-Tyr-<u>Ser</u>-Lys-Asp-Cys-Glu-Gly (SEQ ID NO:7)
Cys-Lys-Arg-Arg-Val-Glu-<u>Ser</u>-Gly-Glu-Gly-<u>Ser</u>-Asp-Arg (SEQ ID NO:8)
<u>Ser</u>-Thr-Glu-Glu-Thr-Glu-Leu-Glu-His (SEQ ID NO:9) and
Ala-<u>Ser</u>-Gln-<u>Ser</u>-Val-Glu-Ile-<u>Ser</u>-Glu-Glu-Pro-Ala-Gln (SEQ ID NO:10).

The p66 dbl peptide sequences having the greatest potential for threonine phosphorylation include those sequences designated SEQ ID NOs: 3–10, where the phosphorylated residues are underlined:

Ser-Pro-Ser-Arg-Asp-Lys-Glu-Glu-Glu-Glu-Glu-Arg-Pro-Gly-<u>Thr</u>(SEQ ID NO:11)

Lys-Lys-Gly-Ala-Thr-Lys-Met-Lys-Asp-Leu-Ala-Arg (SEQ ID NO:12)
Val-Lys-Lys-Arg-Lys-Gln-Gln-Asp-Gln-Leu-Thr-Glu-Arg-Asp-Lys-Phe (SEQ ID NO:13)
and
Ser-Thr-Glu-Glu-Thr-Glu-Leu-Glu-His (SEQ ID NO:14).

The p66 dbl peptide sequence having the greatest potential for tyrosine phosphorylation is:
Glu-Leu-Leu-Lys-Tyr-Ser-Lys-Asp-Cys-Glu-Gly (SEQ ID NO:15).

Some p66 dbl sequences possess a combination of residues containing potential phosphorylation sites for both serine and threonine. Those residues are:
Ser-Pro-Ser-Arg-Asp-Lys-Glu-Glu-Glu-Glu-Glu-Glu-Arg-Pro-Gly-Thr (SEQ ID NO:16)
Ser-Thr-Glu-Glu-Thr-Glu-Leu-Glu-His (SEQ ID NO:17).

One p66 dbl sequences possesses a combination of residues containing both serine and tyrosine:
Glu-Leu-Leu-Lys-Tyr-Ser-Lys-Asp-Cys-Glu-Gly (SEQ ID NO:18).

All possible phosphorylated peptide permutations including those containing phosphorylated threonine and/or tyrosine residues are tested because aberrant phosphorylation might not be confined to serine residues only. The 16 peptides listed above plus others with phosphorylated residues at the additional sites. The additional peptides comprise different phosphorylated/dephosphorylated combinations of those peptides listed above providing that they possess two or more amino acid residues capable of undergoing phosphorylation. The need to analyze each epitope containing a variation in one phosphorylated amino acid within a span of 5 amino acids(ideal epitope size) is predicated by the work of Szendrei (Szendrei et al., Recognition of the minimal epitope of monoclonal antibody Tau-1 depends upon the presence of a phosphate group but not its location. J Neurosci Res 1993;34(2):243–9) who has shown that dephosphorylation of a single amino acid residue prevents specific monoclonal antibody binding of the epitope defined by that residue. Excluded are permutations where phosphorylateable residues are separated from one another by more than six non-phosphorylateable residues (ie. second S and T in peptide SEQ ID NO:16) as these would define two separate and distinct epitope regions. The additional peptides and their derivative constructs include:
Met-Ser-Ser-Gly-Arg-Arg-Gly-Ser (SEQ ID NO:19)
Met-Ser-Ser-Gly-Arg-Arg-Gly-Ser (SEQ ID NO:20)
Met-Ser-Ser-Gly-Arg-Arg-Gly-Ser (SEQ ID NO:21)
Met-Ser-Ser-Gly-Arg-Arg-Gly-Ser (SEQ ID NO:22)
Met-Ser-Ser-Gly-Arg-Arg-Gly-Ser (SEQ ID NO:23)
Met-Ser-Ser-Gly-Arg-Arg-Gly-Ser (SEQ ID NO:24);

Ser-Pro-Ser-Arg-Asp-Lys-Glu-Glu-Glu-Glu-Glu-Glu-Arg-Pro-Gly-Thr(SEQ ID NO:25)
Ser-Pro-Ser-Arg-Asp-Lys-Glu-Glu-Glu-Glu-Glu-Glu-Arg-Pro-Gly-Thr(SEQ ID NO:26);

Cys-Lys-Arg-Arg-Val-Glu-Ser-Gly-Glu-Gly-Ser-Asp-Arg (SEQ ID NO:27)
Cys-Lys-Arg-Arg-Val-Glu-Ser-Gly-Glu-Gly-Ser-Asp-Arg (SEQ ID NO:28);

Ala-Ser-Gln-Ser-Val-Glu-Ile-Ser-Glu-Glu-Pro-Ala-Glu (SEQ ID NO:29)
Ala-Ser-Gln-Ser-Val-Glu-Ile-Ser-Glu-Glu-Pro-Ala-Glu (SEQ ID NO:30)
Ala-Ser-Gln-Ser-Val-Glu-Ile-Ser-Glu-Glu-Pro-Ala-Glu (SEQ ID NO:31)
Ala-Ser-Gln-Ser-Val-Glu-Ile-Ser-Glu-Glu-Pro-Ala-Glu (SEQ ID NO:32)
Ala-Ser-Gln-Ser-Val-Glu-Ile-Ser-Glu-Glu-Pro-Ala-Glu (SEQ ID NO:33)
Ala-Ser-Gln-Ser-Val-Glu-Ile-Ser-Glu-Glu-Pro-Ala-Glu (SEQ ID NO:34);

Ser-Thr-Glu-Glu-Thr-Glu-Leu-Glu-His (SEQ ID NO:35)
Ser-Thr-Glu-Glu-Thr-Glu-Leu-Glu-His (SEQ ID NO:36);

Ser-Thr-Glu-Glu-Thr-Glu-Leu-Glu-His (SEQ ID NO:37);
and
Ser-Thr-Ilu-Glu-Thr-Glu-Leu-Glu-His (SEQ ID NO:38).

Basic techniques pertaining to the synthesis of peptides containing phosphorylated serine, threonine and/or tyrosine residues are well known in the art (Carpenter et al., Phosphoinositide 3-kinase is activated by phosphopeptides that bind to the SH2 domains of the 85-kDa subunit. J Biol Chem 1993;268(13):9478–83; Ottinger et al., Synthesis of phosphotyrosine-containing peptides and their use as substrates for protein tyrosine phosphatases. Biochemistry 1993;32(16):4354–61; Otovos et al., Phosphorylation loops in synthetic peptides of the human neurofilament protein middle-sized subunit. J Protein Chem 1988;7(4):365–76; Andrews et al., Solid-phase synthesis of a range of O-phosphorylated peptides by post-assembly phosphitylation and oxidation. Int J Pept Protein Res 1991;38(5):469–75; Garbay-Jaureguiberry et al., Solid phase synthesis of peptides containing the non-hydrolyzable analog of (O)phosphotyrosine, p(CH2PO3H2)Phe. Application to the synthesis of 344–357 sequences of the beta 2 adrenergic receptor. Int J Pept Protein Res 1992;39(6):523–7; Escobedo et al., A phosphatidylinositol-3 kinase binds to platelet-derived growth factor receptors through a specific receptor sequence containing phosphotyrosine. Mol Cell Biol 1991; 11(2):1125–32; Kwon et al., Stereochemistry specifies the regiochemistry of phosphorylation in two cAMP-dependent protein kinase substrates. J Biol Chem 1993;268(22):16725–9). Peptides containing either single or multiple phosphorylated residues are easily constructed. Purification of individual peptides to >95% purity is accomplished with standard HPLC techniques well known in the art. Qualification of amino acid composition and sequence of individual peptides is performed using well known, standard HPLC plus mass spectroscopy analysis (Garbay-Jaureguiberry et al., Solid phase synthesis of peptides containing the non-hydrolyzable analog of(O)phosphotyrosine, p(CH2PO3H2)Phe. Application to the synthesis of 344–357 sequences of the beta 2 adrenergic receptor. Int J Pept Protein Res 1992;39(6):523–7; Kwon et al., Stereochemistry specifies the regiochemistry of phosphorylation in two cAMP-dependent protein kinase substrates. J Biol Chem 1993;268(22): 16725–9; Stachowiak et al., Peptide mapping using thermospray LC/MS detection: rapid identification of hemoglobin variants. Pept Res 1989;2(4):267; Khandke et al., Influence of ions on cyclization of the amino terminal glutamine residues of tryptic peptides of streptococcal PepM49 protein. Resolution of cyclized peptides by HPLC and characterization by mass spectrometry. Int J Pept Protein Res 1989;34(2): 118–23).

Szendrei has shown that it is possible to detect a single phosphate substitution on epitopes recognized by individual monoclonal antibodies (Szendrei et al., Recognition of the minimal epitope of monoclonal antibody Tau-1 depends upon the presence of a phosphate group but not its location. J Neurosci Res 1993;34(2):243–9). Furthermore, other studies have illustrated that phosphorylation of residues in close proximity to one another can provide epitope-altering conformational changes because of salt bridging by the phosphate molecules (Otovos L Jr., Hollosi M, Perczel A, Dietzschold B, Fasman GD. Phosphorylation loops in synthetic peptides of the human neurofilament protein middle-sized subunit. *J Protein Chem* 1988;7(4):365–76). The epitope-binding sensitivity of individual human serum antibodies is used to determine whether neo-antigenic epitopes composed of aberrantly phosphorylated serine, threonine and/or tyrosine residues exist in p66 dbl.

Peptides designated SEQ ID NOs:3–38 are synthesized, conjugated to HSA and analyzed as set forth above. Briefly, breast cancer and control sera are tested against a mixture of HSA-phosphorylated peptide conjugates. The HSA-peptide mixture is analyzed using a western blot method. A mixture of all possible peptide permutations is employed to identify those sera, cancer and control, reacting with any individual peptide. To minimize non-cancer-specific epitope reactions, each tested serum sample is spiked with the non-phosphorylated equivalents of peptides having SEQ ID NOs:3–10, 12 and 13. Those peptides are conjugated to HSA and used in a mixture to inhibit serum antibodies recognizing the non-specific epitopes of each phosphorylated peptide. Those antibodies (likely in cancer patient sera only) that react with the tumor-specific epitopes are likely left uninhibited. The antibody isotypes tested are IgA, IgG, IgM, and IgE. Individual patients likely produce different reactive antibody isotypes in response to any given immunogenic protein.

The prevalence of IgM production among patients with Stage I disease as compared to Stages II, III and IV would strongly suggest that even earlier detection, at the carcinoma in situ (CIS) stage, might be possible by measuring IgM reactivity. IgE reactivity is analyzed to test the premise that IgG-producing sensitization requires prolonged antigen exposure and therefore not likely to be a useful isotype in early breast cancer detection. Any such reactivity is therefore analyzed in the context of the corresponding stage of breast cancer of the tested serum.

Serum samples from patients with all stages of ductal and lobular carcinoma are tested along with control samples obtained from patients with benign breast lesions and healthy subjects.

All initially reactive patient and control sera are retested against individual HSA-phosphorylated peptide conjugates. Sera reacting in a positive fashion with the mixture of HSA-peptide conjugates is used to test the humoral reactivity of each individual conjugate. The assay methodology remains the same. However, the spiking antigen is, in each case, the corresponding non-phosphorylated HSA conjugate and not the spiking conjugate mixture. Those phosphorylated peptides which react only with breast cancer sera are analyzed further.

The longest possible, breast cancer-specific, amino acid sequence on either side of each aberrantly phosphorylated amino acid residue is mapped out. A successful conclusion of this task provides peptides which function as a cancer-specific immunogens and also serve as ideal source antigen for constructing cancer-specific serum antibody assays without the need of preparative antigen spiking. Delineation of the largest possible cancer-specific immunogenic domain provides enough binding sites for most available serum antibodies to react with even though these can vary ever so slightly in their structural recognition of the phosphorylated residue region. This increases assay sensitivity. Aberrant residue phosphorylation may confer epitope specificity well beyond the 5–6 amino acid reach of the phosphorylated residue. This might occur because of a change in distal peptide conformation brought on by salt bridging between phosphorylated residue and distal amino acids (Otovos et al., Phosphorylation loops in synthetic peptides of the human neurofilament protein middle-sized subunit. *J Protein Chem* 1988;7(4):365–76).

Various shorter versions of the peptides identified as being breast cancer-specific are synthesized and tested against the dbl-positive breast cancer sera and control sera. The control sera tested consist of a statistically significant number of samples obtained from patients with benign breast lesions and from healthy controls. Full length peptides are tested without preparative serum spiking. A finding that the resulting positive reactivity is specific for the cancer sera would confirm total peptide specificity. If the resulting measured reactivity is shared between cancer and control sera, the peptides in question are shortened by two amino acids on one end exceeding 5 amino acids from the nearest phosphorylated residue and then the other. Each new peptide is retested and, if necessary, shortened further until the desired specific antibody reactivity is attained.

The end-result is the acquisition of a library of aberrantly phosphorylated peptides which serve as a source of breast cancer-specific humoral antigens. These antigens can then be used to develop an antibody-based screening assay for detecting early breast cancer.

G. Kit for detecting the presence of tumors

The aspired level of detection is carcinoma-in-situ (C-I-S). What is possible, providing molecules such as p66 dbl are found to identify the other 76% of breast cancer patients, is Stage I detection for which there is no reliable equivalent at the present time.

An ELISA-based, prototype screening assay is provided. Its source antigen is a tumor-specific antigen of this invention. The specific peptides are covalently coupled to HSA to effect reliable microtitre well coating. Each peptide is synthesized with a neutral, non-reactive linker amino acid sequence to facilitate its conjugation to HSA and also to provide it with sufficient projection away from the HSA molecule so as to be optimally available for serum antibody binding. The coating quantity of each conjugate is determined separately in specific optimization experiments. Information derived from quantifying individual antigen coating is used to construct a proportional antigen mixture formula. A mixture of HSAla-peptide conjugates is used in order to provide high sensitivity and specificity.

Antigens derived from a sufficiently large and diverse group of tumor-specific antigens are mixed together. The composition of the peptide-HSA mixture also takes into account which antigens best serve early tumor recognition. Therefore, the immunogenic peptides are screened against early Stage sera and sera from C-I-S patients. Also tested are the individual antibody isotypes to determine which is(are) best suited for early detection.

EXAMPLE 1

Identification of HSTA

The absence of specific, targetable squamous cell carcinoma (SCC) antigen has thus far restricted the development of immunotherapeutic modalities such as vaccination and adoptive transfer of tumor-reactive T cells. In this example it is shown that most SCC patients and control subjects possess serum IgA, IgE and IgG antibodies against SCC cytoplasmic proteins. Some of these proteins appear to serve as highly specific tumor antigens as they couple with high exclusively to patient IgA and IgG antibodies when analyzed by western blot techniques. In this example thirty HSTA tumor antigens are identified. Individual HSTA react with IgA or IgG in different patient sera and in different positive/negative combinations. All patient sera appeared to possess some immunoglobulin reactive with some HSTA while no patient sera contained antibodies reactive to all HSTA. Thus a library of differential SCC antigens can be isolated and expanded from patients.

More specifically, this example shows: (1) the expansion of twenty-five individual SCC lines; (2) the isolation of soluble cytoplasmic proteins and other molecules from a mixture of these cell lines; (3) the conjugation of SCC cytoplasmic proteins to CNBr-activated paper-discs; (4) the testing of various SCC patient and control sera for IgA, IgE and IgG binding to the cytoplasmic antigens; and (5) antigen-inhibition studies to confirm the specificity of each assay. A mixture of monoclonal SCC cell lines of differing tumor origin were used in order to minimize, through dilution, the effect of antigens which were either present in insufficient quantities within each cell type to be sufficiently immunogenic or were present in only a few cell lines and would thus be considered minor or lesser antigens. CNBr-activated paper discs to couple the test antigen were used because they provided coupling of the protein via their free amino groups, thereby avoiding carbohydrates and nucleic acids as antigens. IgA and IgE isotypes were measured along with IgG because their expression by B cells also require T cell co-function.

A. Serum Sample Sources

The sera of sixty-five patients with SCC of the head and neck and sixty-five age and gender matcher controls were analyzes. Twenty-two of the patient sera were from subjects with Stage I or II disease, and forty-three serum samples were from patients with Stage III or IV disease. The control sera sere collected from age and gender-matched subjects who were in good health.

B. Tumor Cell Culture

Twenty-five established SCC cell lines were expanded in approximately equal quantities to provide a combined cell pellet equal to 35 mL. All had been originally derived from tumors of various locations in the head and neck. The cell lines included:
UM1,5,6,8,9,10,11,12,14,15,16,17, and 18 (obtained from Dr. T. Carey, University of Michigan, Ann Arbor), SCC-21, 23,24,25,26,28,29,30,31 (Northwestern University); and HTB-43, CCL-23, and 138 (ATCC, Rockville, Md.).

All cell lines were cultured and expanded with MEM+ NEAA+7% FBS+SerXtend culture media (Culture Facility, U.C.S.F.). At approximately 70% confluence, cell monolayers were lifted from tissue culture flasks for culture expansion purposes or for cytoplasmic protein isolation by treatment with a solution of 0.1% trypsin and 0.4% EDTA in Puck's saline for 5–10 minutes at 37 C. Fresh culture media was then added and the monolayer lightly agitated to release the individual cells. The resulting cell suspension was centrifuged at 1500 RPM, the supernatant aspirated and discarded, and the cell pelleted resuspended in tissue culture media for further expansion or washed twice with PBS (50 mM sodium phosphate, pH 7.3, +150 mM NaCl) for cytoplasmic protein isolation.

C. Isolation of Intracellular Proteins

Washed and pelleted tumor cells were suspended in a solution containing PBS and 1 mM benzamidine, 1 mM EDTA, 1 mM PMSF and 1 mM leupeptin cooled to 4° C. The cell suspension was sonicated for 15 seconds at a setting just high enough to achieve frothing while the mixture was being cooled in an ice water bath. The sonicated suspension was then centrifuged at 100,000 g, 4° C. for sixty minutes. The supernatant was set aside and the cell pellet resuspended. The sonication-centrifugation procedure was repeated seven times. All supernatants were pooled and the final cell pellet, containing cell membranes, intact nuclei and large organelles, were discarded. The pooled supernatant solution was dialyzed against PBS containing three protease inhibitors and using 3,500 MW tubing. The protein content of the processed solution was determined using a Bio-Rad Protein Assay Kit (BioRad, Richmond, Calif.). The solution was then aliquoted. Samples not used immediately were frozen at −20° C.

D. RAST Analysis of Patient and Control Sera

The serum samples were analyzed for specific IgE, Ceska, et al., Allerg. Clain. Immun. 49:1–19 (1972). CNBr-activated paper discs were coupled with 10 micrograms of SCC protein per disc. The anti-serum was $I^{125}$ labelled affinity purified goat anti-human IgE. The serum and anti-serum incubating steps were each extended to twenty hours and the washing buffer changed to PBS containing 0.1% TWEEN20™. The assay system was calibrated with a 25 IU IgE/mL standard, Nalebuff, et al., Carlsbad Calif.: Symposia Foundation 35–48 (1989). Each serum sample (100 microliters per disk) was assayed against the SCC protein-coupled discs and against blank paper discs. The blank paper discs were CNBr-activated discs that had been quenched with 50 mM ethanolamine. Test values greater than or equal to 2.5 standard deviations above the mean background values obtained for the corresponding blank paper discs were considered positive. Blank paper discs were employed as background delineators after it was determined that no difference in the net background existed between them and the SCC protein-coupled discs when both were tested with an excessive quantity of nonspecific IgE (1000 IU/mL of a mixture of human myeloma IgE (Scripps Laboratory, San Diego, Calif.).

E. RAST Inhibition of IgE-Positive Sera

Ten SCC IgE-positive serum samples, randomly selected from among tumor patients and controls, were analyzed by inhibition with SCC intracellular protein. The inhibition solution comprised 2.5 mg/ml SCC protein plus 8% human serum albumin (HSA) in PBS. Each serum sample was serially diluted 1:2 with the SCC antigen solution and also with an 8% HSA/PBS solution alone. Each sample set was incubated for 18 hours at 4° C. before incubation with SCC protein-coupled paper disc. The remaining procedure was unchanged from that used to measure IgE antibody.

F. Determination of Serum IgA and IgG Antibodies Specific or for SCC Cytoplasmic Proteins Serum samples were diluted 1:200 with neat goat serum. Diluted samples were capped and incubated under gentle agitation for four hours at room temperature. 100 microliters of diluted patient or control serum was applied to duplicate SCC cytoplasmic protein-coupled discs and duplicate blank discs. Discs plus sera were incubated at 25°–27° C. for twenty hours. Discs were then washed with 275 microliters of 50 mM PBS, pH 7.3, 0.1% TWEEN20™ (wash buffer) three times. The last wash was left to soak discs for ten minutes. The entire wash cycle was repeated three more times. 50 microliters per disc of $I^{125}$-labelled (Bolton Hunter Method), affinity purified goat anti-human IgA or anti-human IgG (Kirkegaard and Perry, Gaithersburg, Md.) was applied to each disc. (Each radiolabeled antisera was diluted in neat goat serum to achieve 40,000–45,000 counts per minute per 50 microliters of sample. The discs were again incubated at 25°–27° C. for twenty hours, washed in four 10 minute cycles as before and then counted in a gamma counter for two minutes. Specific activity was determined for each analyzed sample by the formula: mean of antigen discs minus (mean+2.5 SD of blank discs)/mean count of 50 microliters of radioisotope solution.

G. RAST Inhibition of IgA, IgG-Positive Sera

Ten SCC IgA-positive serum samples and ten IgG-positive samples, randomly selected from among tumor patients and controls, were analyzed by inhibition with SSC cytoplasmic protein. The inhibiting solution comprised 2.5 mg/mL SCC protein in neat goat serum Each serum sample, already diluted 1:100 in neat goat serum, was diluted 1:2 with SCC antigen solution and also with neat goat serum alone. Each sample set thus processed was incubated for eighteen hours at 4° C. before incubation with SCC protein-coupled paper discs.

The remaining procedure was unchanged from that used to measure IgA and IgG.

H. Ion-Exchange Fractionation of SCC Cytoplasmic Proteins

The cytoplasmic protein mixture derived through the procedure set out in Example 1, part C was dialyzed against 20 mM sodium phosphate buffer, pH 8.2 (3,500 MW pore dialysis tubing). The resulting material was loaded on to a Bio-Rad DEAE semi-prep HPLC column (Bio-Rad, Richmond, Calif.) pre-equilibrated with 20 mM sodium phosphate buffer pH 8.2 (Buffer A). A 12 hours linear, elution gradient was run to reach 100% Buffer B (Buffer A+1M NaCl) at a 2 mL/min flow rate. Approximately seventy-five protein-containing fractions were collected. The flow-through material was then loaded on a Bio-Rad SP ion-exchange column and eluted under similar conditions with twenty-five fractions collected. Then protein content of each fraction was ascertained using a Bio-Rad protein quantification kit, each fraction aliquoted and frozen to −20° C.

I. Screening of Patient and Control Sera Against Fractionated Antigens

CNBr-activated paper discs were incubated with material from each SCC cytoplasmic protein fraction as isolated according to the procedure set out in Example 1, part H equivalent to five micrograms protein per disc and processed as outlines in Example 1, part F. Ten patient and ten control sera were incubated with a disc representative of each eluted fraction and assayed for IgA binding. Another group of 10 patient and 10 control sera were assayed for IgG binding. Each sera was selected because it had registered positive for one or the other when tested against paper discs coupled with the entire cytoplasmic protein mixture. An exception was made in the case of the control sera used in measuring IgA where only one had been positive. All the samples tested together for IgA were assayed in run number 1 and all samples used to measure IgG in run number 2. A median background was determined for each serum sample employing blank paper discs. A score was calculated for each subject fraction value employing blank paper discs. A score was calculated for each subject fraction value employing the formula: fraction value (No.counts)/median patient background (No.counts). A median score was calculated for each fraction comparing SCC patient sera as a group to age and gender matched controls. In order to ascertain which fractions were more likely to have tumor-distinctive proteins, each patient median score corresponding to a particular fraction was subtracted from the corresponding SCC patient score. Those fractions yielding a net positive score were identified for PAGE fractionation and Western blot analysis, as describes in part J.

J. Autoradiographic Western Blots of Fractionated SCC Cytoplasmic Proteins Utilizing Patient and Control Sera SDS-PAGE was carried out according to the method of Laemmli using a ten percent separation gel and a maxi size format (Hoefer Scientific Instruments, San Francisco, Calif.). The dimensions of the separating gel were 142 mm width×140 mm height×1 mm thickness. The sample well width was six mm. Soluble SCC antigen fractions recovered from DEAE ion exchange chromatography were dialyzed (3500 MW pore dialysis tubing) against 1 mM sodium phosphate buffer, pH 7.2 and separated in one mL aliquots in polypropylene tubes. The three enzyme inhibitors were added to each tube (1 mM of each) to minimize degradation of the SCC proteins. All fractions were completely dried using a Speed-Vac (Sarant Instruments, Farmingdale, N.Y.) and thereafter maintained at −20° C. Ten micrograms form each desirable protein fraction was reconstituted, mixed with sample buffer and boiled for four minutes yielding ten microliters of sample loaded per well. Each gel was run initially at twenty mA (constant current) for forty-five minutes until all proteins had entered the separating gel. The current was then raised to 25 MA for approximately three hours or until the bromophenol blue dye had reached the bottom of the gel.

i. Gel Transfer

The gel was removed after electrophoresis and equilibrated in transfer buffer (100 mM Tris-glycine, pH 8.8, 10% methanol) for ten minutes with gentle agitation. A 14×16 cm piece of nitrocellulose paper and six pieces of Whatman number three paper (15×16 cm) were soaked in 1 liter of transfer buffer along with two appropriately sized sponges. The gel was placed in transfer buffer along with the paper and the two sponges. The gel was placed on top of the nitrocellulose paper followed by three pieces of the Whatman paper and a layer of sponge. Three pieces of the Whatman paper and another piece of sponge were then placed on top of the gel. While assembling for transfer care was taken to prevent air bubbles from being trapped between the nitrocellulose paper and the gel. The assembly was emplaced in the transfer chamber and 40 volts (constant voltage) was applied overnight and the next day increased to 400 V for forty-five minutes. Cooling was employed overnight and the next day increased to 400 V for forty-five minutes. Cooling was employed through-out the electrophoresis. Six mm strips corresponding to the electrophoretic pathways were cut employing a no-touch technique and blocked for two hours in a solution of five percent nonfat dry milk, 50 mM PBS and 0.05 percent $NaN_3$ ii. Primary Antibody Step Patient or control sera were diluted 1:200 with neat goat serum containing five percent nonfat dry milk and 0.05 percent $NaN_3$ and agitated gently for two hours at room temperature. Each strip was then incubated with diluted patient serum, control subject serum or diluent alone for twenty hours at room temperature under gentle agitation. Each strip was washed X5 using three mL of PBS containing 0.1 percent TWEEN20™ allowing ten minute soaking intervals between each wash.

iii. Secondary Antibody Step $I^{125}$-labeled affinity purified goat anti-human IgA or IgG (Kirkegaard and Perry, Gaithersburg, Md.) was sufficiently diluted with five percent nonfat day milk, 50 mM PBS, 0.05 percent $NaN_3$ so as to give 50,000 CPM/50 microliters. Each strip was incubated with two milliliters of either labeled anti-IgA or anti-IgG solution for twenty hours, at room temperature. Each strip was then washed five times, dried and exposed on X-ray film for forty-eight hours.

iv. Preparation of HSTA Sensitized Lymphocyte Population from Autologous Peripheral Blood, Lymph Node and Tumor Tissue Freshly drawn, heparinized peripheral blood was obtained from individual SCC patients. The blood was diluted 1:2 with Hank's Balanced Salt Solution (HBSS) and loaded on Ficoll Hypaque density gradient (Hystopaque, Sigma Chemicals, St. Louis). Sample thus prepared were centrifuged at 2,500 rpm for twenty minutes, lymphocyte were recovered from the interface between Ficoll and HBSS, and then washed three times with HBSS. These freshly prepared lymphocytes were resuspended in RPMI 1640 containing thirty percent human AB serum and ten percent DMSO and kept frozen in liquid nitrogen if not used immediately.

Lymph node (LN) tissue was minced and passed through appropriately sized stainless steel mesh to achieve a single cell suspension. The LN lymphocytes were isolated and frozen in liquid nitrogen as described above, if not used immediately.

When thawed, lymphocytes were resuspended in twenty percent AB serum and then washed X3 using RPMI-1640 containing ten percent human AB serum (hereinafter referred to as complete media or CM) to remove DSMO.

L. Generation of Antigen-specific T Cells

Fresh or freshly thawed $2 \times 10^6$ lymphocytes were resuspended in two mL CM and sensitized in vitro with soluble HSTA peptide or protein, each in individual wells of twenty-four well plates at 37° C. in five percent $CO_2$. After four days, one mL of media was removed from each well and replaced with one mL of five micrograms/mL rIL-2. On day eleven, the second in vitro sensitization was undertaken with the antigens, in the presence of irradiated antigen presenting cells (APC) and with a similar quantity of IL-2. APC were homologous PBL (greater than $10^5$) or dendritic cells. After the desired number of antigen/rIL-2 restimulation steps resulted in T cell proliferation, specific target cell killing and/or antigen-specific T cell proliferation assays were carried out.

M. Determination of Antigen-Specific T Cell Responses Using

Proliferation Assays and Chromium Release Assays i. Proliferation assay $10^5$ cells suspended in CM were cultured, in triplicate, for three days in a ninety-six well flat-bottom plate in the presence of five micrograms per mL of specific peptide or peptide mixture with autologous or MHC matched antigen presenting cells. Phytohemagglutinin (PHA) was added in place of specific antigen to the positive control wells and media alone was used in negative control wells. Cells were pulsed with $^3H$ thymidine (0.5 µCi/well) eighteen hours prior to harvesting. Cells were harvested using an automatic harvester and tubes containing individually transferred NYLON (Du Pont) discs for counting in a scintillation counter.

ii. Cytotoxic Assay $1 \times 10^6$ SCC target cells were labelled with 250 µCi of $Cr^{51}$ for sixty minutes at 37° C. SCC target cells were autologous or closely MHC matched. After incubation unbound $Cr^{51}$ was removed by three washed with HBSS. The labelled target cells were mixed with effector cells at various effector to target (E:T) ratios (i.e. 50:1,25:1. 5:1. 1:1). The resulting effector/target cells mixtures were resuspended in 200 microliters CM and centrifuged at 500 rpm for three minutes to effect cell to cell contact. After four hours of incubation, the microliter plates were spun at 1000 rpm for five minutes and 100 microliters of supernatant were removed and counted in a gamma counter.

v. Preparation of Unsensitized Lymphocyte Population from Autologous Peripheral Blood, and/or Lymph Node Freshly drawn, heparinized peripheral blood containing unsensitized lymphocytes was obtained from a SCC patient to undergo treatment. The blood was diluted 1:2 with Hank's Balanced Salt Solution (HBSS) and loaded on Ficoll Hypaque density gradient (Hystopaque, Sigma Chemicals, St. Louis). Sample thus prepared were centrifuged at 2,500 rpm for twenty minutes, lymphocyte were recovered from the interface between Ficoll and HBSS, and then washed three times with HBSS. These freshly prepared lymphocytes were resuspended in RPMI 1640 containing thirty percent human AB serum and ten percent DMSO and kept frozen in liquid nitrogen if not used immediately. Lymph node (LN) tissue was minced and passed through appropriately sized stainless steel mesh to achieve a single cell suspension. The LN lymphocytes were isolated and frozen in liquid nitrogen as described above, if not used immediately.

When thawed, lymphocytes were resuspended in twenty percent AB serum and then washed X3 using RPMI-1640 containing ten percent human AB serum (hereinafter referred to as complete media or CM) to remove DSMO.

Generation of Antigen-specific T Cells

Fresh or freshly thawed $2 \times 10^6$ lymphocytes were resuspended in two mL CM and sensitized in vitro with soluble HSTA peptide or protein, each in individual wells of twenty-four well plates at 37° C. in five percent $CO_2$. After four days, one mL of media was removed from each well and replaced with one mL of five micrograms/mL rIL-2. On day eleven, the second in vitro sensitization was undertaken with the antigens, in the presence of irradiated antigen presenting cells (APC) and with a similar quantity of IL-2. APC were homologous PBL (greater than $10^5$) or dendritic cells. After the desired number of antigen/rIL-2 restimulation steps resulted in T cell proliferation, specific target cell killing and/or antigen-specific T cell proliferation assays were carried out.

Determination of Antigen-Specific T Cell Responses Using Proliferation Assays and Chromium Release Assays Proliferation assay $10^5$ cells suspended in CM were cultured, in triplicate, for three days in a ninety-six well flat-bottom plate in the presence of five micrograms per mL of specific peptide or peptide mixture with autologous or MHC matched antigen presenting cells. Phytohemagglutinin (PHA) was added in place of specific antigen to the positive control wells and media alone was used in negative control wells. Cells were pulsed with $^3H$ thymidine (0.5 µCi/well) eighteen hours prior to harvesting. Cells were harvested using an automatic harvester and tubes containing individually transferred NYLON (Du Pont) discs for counting in a scintillation counter.

Cytotoxic Assay $1 \times 10^6$ SCC target cells were labelled with 250 µCi of $Cr^{51}$ for sixty minutes at 37° C. SCC target cells were autologous or closely MHC matched. After incubation unbound $Cr^{51}$ was removed by three washed with HBSS. The labelled target cells were mixed with effector cells at various effector to target (E:T) ratios (i.e. 50:1,25:1. 5:1. 1:1). The resulting effector/target cells mixtures were resuspended in 200 microliters CM and centrifuged at 500 rpm for three minutes to effect cell to cell contact. After four hours of incubation, the microliter plates were spun at 1000 rpm for five minutes and 100 microliters of supernatant were removed and counted in a gamma counter.

Results

A majority of patients and control subjects (40/65 and 46/65 respectively) possessed either IgA, IgE or IgG intracellular SCC protein-specific antibodies in their sera. Thirty of the 65 cancer patients and 40 of the 65 controls were IgE positive. See FIG. 1. Eighteen of the 65 patients but only one of the 65 control sera were IgA-positive. See FIG. 2. Seventeen of 65 patient and 14 control sera were IgG-positive. No statistical difference in IgE and/or IgG antibody-positive prevalence was found between SCC patients and controls, male and female subjects. Additionally, no statistical difference were noted in the mean IgE and or IgG values between the various subject categories that were studied. The IgA-positive prevalence overwhelming favored the SCC group (27.7%0 over the control group (1.5%). An interesting corollary observation was the apparent inverse relationship among patients and controls between the ability to produce IgE and the production of IgA and/or IgG against SCC intracellular antigens (FIGS. 3a,b). All antibody isotype inhibition studies were positive, indicating a high probability of specific antigen/antibody coupling and, therefore, a high degree of individual assay specificity. This is illustrated for one such patient by FIG. 4.

This study demonstrated the presence of a significant humoral immune response targeted against intracellular proteins of squamous cell carcinoma. Also recognized was that antibodies exist to self proteins in the sera of most patient and control subjects. Although the function of these antibodies is unknown, some fundamental conclusions as to their nature are possible. First, it is likely that most IgE and IgG antibodies recognize intracellular proteins common to both SCC and normal cells given the equivalent antibody-positive prevalence and group mean serum antibody values common to both subject groups. Second, the much higher IgA-positive prevalence of the SCC group indicates that some SCC intracellular proteins are not adequately represented in normal cells.

The anti-self antibodies could be part of a normal, homeostatic mechanism such as the binding of intracellular molecules released during normal cell turnover. The coupling of antibody with self-antigen may sustain the clearance of cellular debris by its incorporation into immune complexes and the binding of these immune complexes to Fc or complement receptors of macrophages and other scavenger cells. At times of increased cell death, this process could be deleterious if an inordinately high number of immune complexes form and are deposited onto normal tissues in a widespread and nonspecific way. Alternatively, the self-antigen binding process might be advantageous to SCC patient survival if the increase in immune complex precipitation and/or complement fixation preferentially occurred at the site of tumor thereby resulting in a higher degree of site-situated inflammation followed by anti-tumor immune reactivity. The latter could be mediated by intracellular SCC antigen-driven T cells.

Additionally, observations resulting from this study were (1) that anti-self IgE exists in the sera of most subjects and (2) that an inverse relationship exists between the production of IgE and that of IgA or IgG antibodies. The identification of IgE specific or self-proteins runs counter to our current understanding of IgE function. In the classical Type I immune reaction, IgE is produced in response to immunization by foreign proteins and, to a lesser degree, by haptenized smaller molecules such as penicillin. Most IgE circulates freely. A lesser amount (less than 0.01% of total body IgE) is bound, by specific Fc receptors, to basophil and mast cell surface membranes. Exposure to specific antigen (allergen) leads to multimeric binding of IgE to antigen and of the antigen-IgE antibody complexes to mast cells. The binding of such complexes results in mast cell degranulation and the release of vasoactive and chemotactic molecules. With significant quantities of IgE and the concomitant presence of intracellular SCC antigens (as a consequence of constant cell turnover), a prominent, self-directed hypersensitivity reaction, such as anaphylaxis, should occur in IgE-positive tumor patients but apparently does not. By comparison, possessing similar levels of specific IgE in the presence of antigens of external origin such as bee venom can result in severe and potentially fatal allergic reactions.

It is possible that another and totally different IgE-mediated immune response exists which, because it is internally targeted, promotes normal homeostatic functions. One possible function may be the down-regulation of auto-immune phenomenon in that the production of IgE may be an active component of an immune pathway which bypasses or slows down the production of anti-self IgA and/or IgG. This may be part of a checks and balances system necessary to prevent the conversion of a well regulated IgA, IgG anti-self antibody response to one that is elevated and uncontrolled. In some patients, where the IgE response may be overwhelmingly strong, such down-regulation of immune function may carry over during tumorigenesis wherein anti-tumor immune surveillance is compromised and tumor growth is unchecked. This may explain the reason behind a now old observation of Berczi (Berczi, L, Holford, S. V. Warsi, Z. H., McMorris, L. S., Thorlakson, R. H., Thorlakson, T. K., Sehon, A. H.: Tumor-reactive IgE antibodies in plasma of patients with gastrointestinal carcinomas. *Cancer Immunol. Immunother* 1983; 14(3):180–4) wherein he noted a deleterious effect upon survival for those tumor patients who possess high serum levels of anti-self IgE.

The most fundamental conclusion of this study was, however, that SCC-associated intracellular antigens recognized by host T lymphocytes exist (this holds true because the presence of serum IgA, IgE or IgG antibodies requires antigen-specific helper cell cognate function in the production of those antibody isotypes), are released into the tumor periphery in significant quantities, and, if properly processed, might serve to generate autologous anti-tumor effector cells.

(b) This study has shown that a significant number of SCC intracellular proteins bind with high exclusivity to IgA and IgG antibodies of SCC patients and are thus termed highly specific tumor antigens (HSTA). The HSTA were identified through a series of isolation steps which comprised: (1) the sub-fractionation, by ion-exchange chromatography, of the SCC intracellular protein mixture into 100 sub-mixtures based on the isoelectric point differences of the constituent molecules; (2) coupling of representative quantities of each sub-mixture to CNBr-activated paper discs; (3) utilization of the individual discs to test patient and control sera to determine IgA and IgG antibody binding; (4) selection of the SCC intracellular protein sub mixtures whose corresponding paper discs resulted in higher IgA and/or IgG binding among tumor patient sera; (5) utilization of polyacrylamide gel electrophoresis (PAGE) to separate individual molecules within each preferred sub-mixture; (6) autoradiographic western blotting to identify which individual proteins reacted preferentially with IgA or IgG in patient sera; and (7)

selection as HSTA of molecules which reacted with IgA or IgG of SCC patient sera but not with control sera.

This study provided thirty HSTA on the basis of distinctive patient IgA or IgG binding. Those that bound IgA (FIGS. 5A and 5B) appeared to be more promising antigen candidates as they were recognized with a higher frequency among the individual tumor patient sera than were the molecules which bound patient IgG. The HSTA appeared to be constituted primarily of protein based on their CNBr and Coomassie-Blue-binding characteristics. Molecules that reacted with antibodies from both patients and controls were twice as numerous as HSTA. The combination of all IgA and IgG-reactive molecules was still less numerous (less than 25 percent) than of all protein molecules identified by PAGE with Coomassie staining, implying that not all molecules residing internal to the cell membrane may be immunogenic to patients or controls.

The sizes of most SCC HSTA were between 50,000 and 80,000 (dalton) MW. One HSTA (35.1) was of interest because it bound IgA in all ten SCC patient sera tested without binding antibody in the ten control sera. Other HSTA (3.3, 27.3, 37.2, 39.1, 39.2, 39.4, 40.3, 47.3, 47.4, 49.2, 50.1 and 50.2) individually reacted with IgA in different patient serum combinations. These were of also interest because they, too, afforded 100 per cent SCC patient identification with absolute specificity when their western blot results were summated (FIGS. 5A and 5B).

One HSTA 3.3 has been partially sequenced by standard techniques and was found to have the partial sequence set out in sequence Id. no. 1. This peptide matched with the E6 protein of human papillomavirus. The E6 protein is an oncogene product that functions to promote tumors.

Background

The great majority of autologous antigens are intracellular, are broadly distributed and appear to be proteins. These antigens are expressed both in tumor cells and normal cells as described in immunohistochemistry-based studies. (Pfaff et al., Human monoclonal antibody against a tissue polypeptide antigen-related protein from a patient with a signet-ring cell carcinoma of the stomach. Cancer Res 1990;50(16):5192–8; Abe et al., Human monoclonal antibodies against cytokeratin 18 generated from patients with gastric cancer. Jpn J Cancer Res 1989;80(3):271–6; Furukawa et al., Two human monoclonal antibodies reacting with the major gangliosides of human melanomas and comparison with corresponding mouse monoclonal antibodies. Cancer Res 1989;49(1):191–6; Skaletsky et al., A human monoclonal antibody to cytokeratin intermediate filament antigens derived from a tumor draining lymph node. Hybridoma 1988;7(4):367–76; Imam A, Mitchell M S, Modlin R L, Taylor C R, Kempf R A, Kan M J. Human monoclonal antibodies that distinguish cutaneous malignant melanomas from benign nevi in fixed tissue sections. J Invest Dermatol 1986;86(2):145–8; Pickering J W, Misra R P. Human monoclonal antibodies to cytokeratins associated with squamous cell carcinoma. Clin Immunol Immunopath 1984;32:253–60).

Most human monoclonal antibodies which target surface membrane antigens are of the IgM isotype. (Pigatto et al., Occupational dermatitis in bakers: a clue for atopic contact dermatitis. Contact Dermatitis 1988;16(5):263–71; Jansson et al., The human repertoire of antibody specificities against Thomsen-Friedenreich and Tn-carcinoma-associated antigens as defined by human monoclonal antibodies. Cancer Immunol Immunother 1992;34(5):294–8; Imam et al., Generation and immunohistological characterization of human monoclonal antibodies to mammary carcinoma cells. Cancer Res 1985;45(1):263–71; and Houghton et al., Detection of cell surface and intracellular antigens by human monoclonal antibodies. Hybrid cell lines derived from lymphocytes of patients with malignant melanoma. J Exp Med 1983; 158(1):53–65). Most targeted cell surface antigens are found to be carbohydrates (Furukawa et al., Two human monoclonal antibodies reacting with the major gangliosides of human melanomas and comparison with corresponding mouse monoclonal antibodies. Cancer Res 1989;49(1):191–6; Miyake et al., First establishment of a human monoclonal antibody directed to sulfated glycosphingolipids SM4s-Gal and SM4g, from a patient with lung cancer. Cancer Res 1992;52(8):2292–7; Dan et al., Human antiglioma monoclonal antibodies from patients with astrocytic tumors. J Neurosurg 1992;76(4):660–9).

Although fewer corresponding intracellular antigens bound by human monoclonal IgG have been characterized, it is reasonable to speculate that most must be proteins as IgG expression requires proximal T helper cell cofunction (Sen et al., T cell surface molecules regulating noncognate B lymphocyte activation. Role of CD2 and LFAla-1. J Immunol 1992; 148(4):1037–42). T helper cells cause IgM-producing B cells to switch to isotypes IgA, IgE and/or IgG. T helper cells, in turn, only recognize protein (peptide) antigens.

Some autologous antigens are detected by immunohistochemistry in tumor cells but not in normal cells (Imam et al., Generation and immunohistological characterization of human monoclonal antibodies to mammary carcinoma cells. Cancer Res 1985;45(1):263–71; McKnight et al., Human monoclonal antibodies to nuclear antigens. Hum Antibodies Hybridomas 1990;1(2):77–82; Werner et al., Human monoclonal antibodies directed against ovarian carcinoma. Gynecol Oncol 1989;34(2):148–54; Kan et al., Human monoclonal antibodies directed against melanoma tumor-associated antigens. Cancer Res 1986;46(5):2490–6). These studies suggest that some intracellular tumor-cell molecules are absent from normal cells or are present in reduced quantities within normal cells. Thus, these may serve as tumor-selective immunogens. Such molecules could include malignant transformation antigens (Kan et al., Tumor-reactive human immunoglobulin G monoclonal antibody from a melanoma patient. Cancer Res 1989;49(16):4536–41; Vollmers et al., SC-1, a functional human monoclonal antibody against autologous stomach carcinoma cells. Cancer Res 1989;49(9):2471–6) protein molecules associated with cellular proliferation and regulation of proliferation such as p53 (Labrecque et al., Analysis of the anti-p53 antibody response in cancer patients. Cancer Res 1993;53:3468–3471) fusion proteins such as bcr-abl (Vollmers et al., SC-1, a functional human monoclonal antibody against autologous stomach carcinoma cells. Cancer Res 1989;49(9):2471–6; Chen et al., T-cell immunity to the joining region of p210BCArg-ABL protein. Proc Natl Acad Sci U S A 1992;89(4):1468–72) oncogene expression products such as myb and myc (Ben-Mahrez et al., Circulating antibodies against c-myc oncogene product in sera of colorectal cancer patients. Int J Cancer 1990;46(1):35–8; Sorokine et al., Presence of circulating anti-c-myb oncogene product antibodies in human sera. Int J Cancer 1991;47(5):665–9) and incompletely synthesized molecules such as the core protein of breast mucin (Barnd et al., Specific, major histocompatibility complex-unrestricted recognition of tumor-associated mucins by human cytotoxic T cells. Proc Natl Acad Sci U S A 1989;86(18):7159–63). The qualitative or quantitative presence of tumor-distinct molecules is likely to result from a high degree of cancer cell proliferation, de-differentiation, genetic instability and dyscoordination of metabolic processes.

Autologous antigens which appear highly tumor-specific as visualized by immunohistochemistry can be recognized by monoclonal antibodies expressed from both patient and normal B lymphocytes (Posner et al., An IgG human monoclonal antibody reactive with a surface membrane antigen expressed on malignant breast cancer cells. *Hum Antibodies Hybridomas* 1991;2(2):74–83). In this citation, the author described the generation of human monoclonal antibodies reacting exclusively with intracellular antigens of leukemia cells but derived from normal subject, EBV-transformed B lymphocytes.

EXAMPLE 2

Breast Cancer Specific Humoral Antigens

Potential breast cancer specific proteins were selected on the basis of their individual functional differences and availability. The molecules tested were dbl, erbB-1, erbB-2 (HER-2/neu), erbB-3, fos, HSP70, jun, lck, lyn, p13, p190, rapGAP, ras, rasGAP, and yes.

Some of these proteins were known to be highly associated with breast cancer (erbB-2, fos, jun, and ras). Some were likely not associated with breast cancer cells (dbl, erbB-3, lck, lyn, and yes) and were selected to serve as controls in case all members of the first sub-group were antibody-reactive. Some were found with equal frequency in cancer and in normal epithelium (erbB-1, HSP70, p13, p190, rapGAP, and rasGAP). These were selected in order to determine if serum antibodies specifically-reactive to normally occurring intracellular proteins routinely exist among subjects with or without breast cancer. Some were found in different cellular compartments or structures: cell membrane (dbl, erbB-1, erbB-2, and erbB-3); cytosol (dbl, HSP70, lck, lyn, p190, rapGAP, ras, rasGAP, and yes); or nucleus (fos, jun, and p13). Some possessed different functions which could effect their immunogenic potential: cell membrane receptors (erbB-1, erbB-2, and erbB-3), kinases or kinase effectors (dbl, lck, lyn, p190, rapGAP, ras, rasGAP and yes), response regulators (fos, jun, and p13), or other (HSP70). Some had both an intracellular and extracellular component (erbB-1, erbB-2 and erbB-3). These were of interest because, if antibody-reactive, they could provide a convenient vehicle for testing our premise that proteins, or portions thereof, which are intracellular have the ability to initiate immune recognition whereas those that are extracellular do not. Or, if extracellular domains of membrane proteins were antibody-reactive, their degree of reactivity was much less than for their internal portions. Toward this end, we had available the extracellular domain of erbB-2 with which to test those sera which reacted positive to the entire erbB-2 molecule. Preliminary results indicated that erbB-2 (Disis et al., Existent T cell and antibody immunity to her-2/neu protein in patients with breast cancer, *Cancer Res.*, 1993) and p21 ras (Huseby et al., Detection of antibody responses to ras proteins in patients with colon cancer, *Cancer Res.*, 1993) might serve as a humoral immunogens.

Autoradiographic western blot analysis was used to measure specific humoral immune reactivity among breast cancer patients and patients with benign breast lesions. This method measured serum IgA reactivity to the sixteen proteins tested. IgA was measured because of its higher prevalence in our prior SCC study. The screening sera was obtained from 15 female patients with ductal breast cancer and 15 age-matched female patients with benign breast lesions (fibroadenoma or fibrocystic disease). By using the control sera thus selected, an attempt was made to delineate whether any measured protein-specific antibody reactivity in breast cancer sera was tumor-specific.

The proteins tested were provided in various ways. Some, were recombinant proteins produced in microbial or insect cell expression systems: fos, HSP70, jun, lck, lyn, p13, p190, rapGAP, ras, rasGAP, and yes. (Appendix IV) Others, dbl, erbB-1, erbB-2, and erbB-3, were expressed in NIH/3T3 transfected cell lines (Di-Fiore et al., erbB-2 is a potent oncogene when overexpressed in NIH/3T3 cells, *Science*, 1987;237(4811):178–82; Eva et al., The predicted DBL oncogene product defines a distinct class of transforming proteins, *Proc. Natl. Acad. Sci. USA*, 1988;85(7):2061–5). The latter were semi-purified from individually cultured and homogenized NIH/3T3 transfectants. Briefly, individual transfected cell lines were cultured, washed X3 with 20 mM Tris-HCl, pH 8.5, cooled in an ice bath, homogenized by sonication, and centrifuged. In the case of the erbB receptors, each was then extracted from the post-sonication precipitate with 0.1% SDS followed by precipitation with acetone in three consecutive steps: 25, 50, and 85 percent acetone. Each erbB protein was found in the 50 percent acetone precipitate. In the case of dbl, the aqueous soluble fraction was precipitated under the same conditions but was recovered in the 85 percent acetone precipitate.

The oncogene-encoded protein dbl appears to function as a molecule selectively immunogenic for breast cancer. As depicted in FIG. 6, thirteen proteins reacted with serum IgA antibodies. The non-reactive proteins were erbB-1, erbB-3 and lck. Of the positive reactants, dbl appeared to be the most specific (6/15 positive cancer patient sera versus 1/15 positive benign lesion sera). The remaining IgA-reactive proteins were not significantly more positive when tested with breast cancer patient sera than with benign patient sera. This was especially true for the proteins erbB-2, fos, jun, and ras which have been documented to play an oncogenic role in breast cancer.

All of the proteins commonly expressed in both breast cancer cells and normal epithelium were equally serum antibody-reactive. This substantiated the earlier observation from our squamous cell carcinoma study regarding the universal presence of autologous serum antibodies specific for cytoplasmic proteins.

Some proteins, previously thought to be unexpressed by breast cancer cells, were antibody reactive (dbl, fyn, lyn and yes) while others were not (erbB-3, lck). A case could be made for dbl involvement in breast cancer given its higher antibody positive prevalence which favored the breast cancer patient sera. The hematopoietic proteins fyn, lyn and yes reacted equally with both cancer patient sera and control sera suggesting that these were unlikely to be tumor-specific immunogens in other malignant lesions.

A significant difference in reactivity existed between the inner and outer domains of erbB-2. Of the three epidermal growth factor receptors tested, only erbB-2 was antibody-reactive (4/15 positive cancer patient sera versus 2/15 positive benign lesion sera). This may have been due to its higher quantitative association with breast cancer lesions. However, the six erbB-2-positive sera tested negative against the extracellular domain of erbB-2. This data strengthened or view that sequestration of intracellular self-proteins from immune surveillance behind the confines of the cell membrane is a key component of their immunogenicity. Excluding the membrane receptor group, there was, however, no apparent difference in immunogenic potential between proteins residing in the different intracellular compartments. Nor was there a difference among proteins based upon their intracellular function.

Dbl was also tested for IgG-specific reactivity to determine whether its selectivity for breast cancer could be maintained. 3/15 breast cancer sera were IgG-reactive as compared to 1/15 benign lesion sera. The combined IgA+ IgG reactivity with dbl was 6/15 positive breast cancer sera versus 2/15 for the benign lesion sera. We were able to quantify the degree of positive reactivity for each antibody/ dbl interaction using a Fuji BAS 2000 laser scanning system (Fuji Film Co., Tokyo, Japan). As depicted in FIG. 7, 4/15 breast cancer patient sera were strongly positive and two were weakly positive for IgA+IgG as compared to only two weakly positive values for the benign breast lesion group.

EXAMPLE 3

Phosphorylated forms of dbl serve as breast cancer specific humoral antigens Phosphorylated and non-phosphorylated versions of dbl were purified. The work of Graziani et al. (Graziani G, Ron D, Eva A, Srivastava S K. The human dbl-proto-oncogene product is a cytoplasmic phosphoprotein which is associated with the cytoskeletal matrix. *Oncogene* 1989;4(7):823–9) showed that the p66 dbl oncogene product was significantly more phosphorylated than the normally expected p115 dbl proto-oncogene product. Not only was the p66 form likely to be more quantitatively expressed in breast cancer than in normal cells but it was also qualitatively distinct as compared to its normal p115 homologue.

Two versions of p66 dbl were separately purified by employing the aqueous homogenate from dbl-transfected NIH/3T3 cells as before followed by DEAE and SP ion exchange HPLC chromatography. Minimally phosphorylated or non-phosphorylated p66 dbl was isolated in the follow-through fraction following both DEAE and SP ion exchange chromatography. Heavily phosphorylated dbl was present in DEAE ion exchange fractions eluted at approximately 13 to 21 percent NaCl.

Non-phosphorylated dbl reacted equally with breast cancer sera cancer and control sera. The original 30 sera panel was utilized to test IgA antibody reactivity. The results revealed equivalent reactivity between the benign lesion patient sera and the cancer patient sera (FIG. 8). Ten of 15 breast cancer sera and 8 of 15 benign breast lesion sera were positive.

Phosphorylated dbl reacted more significantly with breast cancer sera than with benign lesion sera. Eight of 15 breast cancer sera were IgA reaction-positive compared to 4 of 15 for the control group (FIG. 9). While all six originally positive breast cancer sera were still positive, two additional positive results were added from the latest study. Two additional positive results were also added from testing the benign lesion sera. These latter results raised the possibility that the p66 dbl antigen we were using was heterogeneous, composed of several versions; some versions could be aberrantly phosphorylated and some normally phosphorylated; some versions could be more tumor-specific and others were less tumor-specific; some p66 dbl versions could be those with phosphorylation at peptide sites matching those found on the p115 proto-oncogene; those possessing p115 phosphorylated sites plus de-novo, aberrantly phosphorylated sites; or those with de-novo phosphorylated sites only.

If the non-specific reactions corresponding to p66 dbl peptide epitopes uninvolved with phosphorylation could be neutralized then those matching the p115 phosphorylation sites (phosphorylated or non-phosphorylated) and/or those corresponding to the de-novo phosphorylated sites but not themselves phosphorylated, perhaps more tumor-specific results could be obtained. This would occur because the antigenic epitopes remaining would be the aberrantly phosphorylated sites.

The reactions corresponding to the p115 phosphorylated sites could likely not be phosphorylated. Those corresponding to dbl peptide epitopes uninvolved with phosphorylation and those matching non-phosphorylated p115 and/or non-phosphorylated de-novo p66 phosphorylation sites could be neutralized, however. Spiking the test sera with non-phosphorylated p66 dbl would likely serve that purpose. The 8 positive cancer patient sera and 4 positive benign lesion patient sera were therefore retested using increasing quantities of non-phosphorylated dbl. Maximum signal inhibition occurred when spiking with 4 μg non-phosphorylated dbl per 200 μl diluted serum sample. At that point, all control sera IgA reactivity ceased while 4 breast cancer sera still remained positive. Increasing the spiking antigen to 10 μg failed to abrogate the IgA reactivity of the remaining positive breast cancer sera. Of the four remaining IgA-positive sera, two were those which had been IgA-positive in the preliminary dbl studies.

Larger numbers of breast cancer patient sera and control sera were tested employing an optimized dbl western blot assay. This more specific dbl assay was used to test 59 breast cancer sera, 27 sera from patients with benign breast lesions, and 36 sera from healthy aged-matched female controls. Positive IgA or IgG antibody reactivity to phosphorylated dbl was found in 14 of 59 breast cancer patient sera (24%), 1 of 27 benign breast lesion patient sera (4%) and 1 of 36 healthy female control sera (3%). Most dbl-reactive sera were either IgA-positive (10/16) or IgG-positive (4/16). Two patient sera were both IgA and IgG-reactive.

Aberrantly phosphorylated dbl reacted equally with sera from patients with Stage I or Stage II ductal carcinoma (FIG. 9). Four of 20 Stage I patient sera (20%) were dbl-reactive; 7 of 29 Stage II sera (24%) were reactive; 1 of 3 Stage III sera were reactive; and 1 of 2 Stage IV sera were reactive. Furthermore, 1 of 5 sera from patients with lobular carcinoma was also positive. The positive serum was obtained from a patient with Stage I disease suggesting that an early humoral immune response is stimulated by antigens closely associated with breast cancer. It also likely to even detect a much earlier immune response, perhaps at the carcinoma in-situ stage if one were to measure an IgM response to the aberrantly phosphorylated peptide regions of dbl and/or other oncogene-encoded proteins. If a strong IgA and/or IgG response is seen in Stage I patient sera, the precursor isotype, IgM could likely be measured even earlier.

Examples have been included to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

The references cited in the specification are incorporated herein by reference to the extent that they supplement, explain, provide a background for or teach methodology, techniques and/or compositions employed herein.

What is claimed is:

1. A process of making a peptide library of tumor specific antigens said process comprising the steps of:
   a) obtaining a plurality of phosphorylated proteins present in tumor cells, said proteins each specifically immunoreacting with tumor patient sera;
   b) identifying in each of said phosphorylated proteins one or more epitopes that specifically immunoreact with tumor patient sera;
   c) obtaining for each epitope a peptide that contains said epitope, and is phosphorylated; and
   d) forming a library of said peptides.

2. The process of claim 1 wherein obtaining comprises the steps of:
   a) extracting proteins from a tumor cell;
   b) screening control and tumor patient sera to determine which of said proteins specifically immunoreact with an antibody in tumor patient sera; and
   c) isolating and purifying said selectively immunogenic proteins.

3. A library prepared by the process of claim 1.

4. A process of making a peptide library of breast cancer specific antigens comprising the steps of:
   a) identifying proteins present in breast cancer cells that each specifically react with sera from breast cancer patients;
   b) defining potential phosphorylation sites of said proteins;
   c) obtaining peptides comprising a portion of said proteins, which portion contains at least one of said phosphorylation sites and wherein at least one of said phosphorylation sites is phosphorylated;
   d) screening said peptides to identify phosphorylated peptides that specifically immunoreact with sera from breast cancer patients; and
   e) forming a library of said phosphorylated peptides.

5. The process of claim 4 wherein said proteins comprise dbl.

6. The process of claim 4 wherein said potential phosphorylation sites comprise:
   a) a phosphorylated serine residue at amino acid residue position number 2, 3, 9, 23, 25, 47, 151, 202, 295, 299, 402, 436, 438, or 442 of SEQ ID NO:2;
   b) at least two phosphorylated serine residues located at amino acid residue position numbers 2 and 3, 2 and 9, 3 and 9, 23 and 25, 295 and 299, 436 and 438, 436 and 442, or 438 and 442 of SEQ ID NO:2;
   c) at least three phosphorylated serine residues located at amino acid residue position numbers 2, 3 and 9 or 436, 438 and 442 of SEQ ID NO:2;
   d) a phosphorylated threonine residue located at amino acid residue position number 38, 263, 380, 403 or 406 of SEQ ID NO:2;
   e) at least two phosphorylated threonine residues located at amino acid residue position numbers 403 and 406 of SEQ ID NO:2;
   f) at least one phosphorylated tyrosine residue located at amino acid residue position number 201 of SEQ ID NO:2;
   g) at least one phosphorylated serine residue and at least one phosphorylated threonine residue wherein
      i) the phosphorylated serine residue is located at amino acid residue position numbers 23 and 25 of SEQ ID NO:2 and one phosphorylated threonine residue is located at amino acid residue position number 38;
      ii) one phosphorylated serine residue is located at amino acid residue position number 402 of SEQ ID NO:2 and two phosphorylated threonine residues are located at amino acid residue position numbers 403 and 406 of SEQ ID NO:2; or
      iii) one phosphorylated serine residue is located at amino acid residue position number 402 of SEQ ID NO:2 and one phosphorylated threonine residue is located at amino acid residue position number 403 or 406 of SEQ ID NO:2; or
   h) at least one phosphorylated serine residue and at least one phosphorylated tyrosine residue wherein said phosphorylated serine residue is located at amino acid residue position number 202 of SEQ ID NO:2 and said phosphorylated tyrosine residue is located at amino acid residue position number 201 of SEQ ID NO:2.

7. The process of claim 4 wherein said portion comprises the amino acid residue sequence of SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38.

8. The process of claim 4 wherein said protein is an oncogene-expression product a cell-cycle protein, a receptor, a transcription factor or other regulatory protein or substrate protein or.

9. A library prepared by the process of claim 5.

10. An assay kit for diagnosing the presence of a tumor in a subject, said kit comprising a peptide library of a plurality of phosphorylated tumor specific antigens and means for detecting the presence in a biological fluid of an antibody immunoreactive with the tumor specific phosphorylated antigens.

11. The kit of claim 10 wherein the tumor is breast cancer and the library comprises a plurality of two or more of said peptides selected from the group consisting of SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 and 38.

* * * * *